(12) United States Patent
Reo

(10) Patent No.: US 7,063,703 B2
(45) Date of Patent: Jun. 20, 2006

(54) SLIP-FIT HANDLE FOR HAND-HELD INSTRUMENTS THAT ACCESS INTERIOR BODY REGIONS

(75) Inventor: Michael L Reo, Redwood City, CA (US)

(73) Assignee: Kyphon Inc., Sunnyvale, CA (US)

( * ) Notice: Subject to any disclaimer, the term of this patent is extended or adjusted under 35 U.S.C. 154(b) by 318 days.

(21) Appl. No.: 10/227,714

(22) Filed: Aug. 26, 2002

(65) Prior Publication Data

US 2003/0004530 A1 Jan. 2, 2003

Related U.S. Application Data

(62) Division of application No. 09/014,229, filed on Jan. 27, 1998, now Pat. No. 6,468,279.

(51) Int. Cl.
*A61B 17/16* (2006.01)

(52) U.S. Cl. .................. 606/79; 606/80; 606/104; 600/567; 81/489

(58) Field of Classification Search .............. 606/79, 606/80, 104; 600/566, 567, 585; 81/489
See application file for complete search history.

(56) References Cited

U.S. PATENT DOCUMENTS

| 931,327 | A | 8/1909 | Manzel |
|---|---|---|---|
| 2,198,666 | A | 4/1940 | Gruskin |
| D149,843 | S | 6/1948 | Ruger |
| 2,709,600 | A | 5/1955 | Lehde |
| 2,919,692 | A | 6/1960 | Ackermann |
| 3,628,524 | A | 12/1971 | Jamshidi |
| 4,013,080 | A | 3/1977 | Froning |
| 4,187,607 | A | 2/1980 | Simuro et al. |
| 4,262,676 | A | 4/1981 | Jamshidi |
| 4,469,109 | A | * 9/1984 | Mehl .................. 600/566 |
| 4,513,754 | A | * 4/1985 | Lee .................... 600/566 |
| 4,630,616 | A | 12/1986 | Tretinyak |
| 4,793,363 | A | 12/1988 | Ausherman et al. |
| 4,838,282 | A | 6/1989 | Strasser et al. |
| 4,938,743 | A | 7/1990 | Lee |
| 4,967,435 | A | 11/1990 | Seals |
| 4,995,872 | A | 2/1991 | Ferrara |
| 5,086,674 | A | 2/1992 | Her |
| 5,178,267 | A | 1/1993 | Grabenkort et al. |
| 5,257,632 | A | 11/1993 | Turkel et al. |
| 5,368,046 | A | 11/1994 | Scarfone et al. |
| 5,385,151 | A | 1/1995 | Scarfone et al. |
| D358,645 | S | 5/1995 | Ryan et al. |
| 5,423,824 | A | 6/1995 | Akerfeldt et al. |
| 5,480,166 | A | 1/1996 | Milsop |
| 5,494,382 | A | 2/1996 | Kloppers |
| 5,522,398 | A | 6/1996 | Goldenberg et al. |

(Continued)

FOREIGN PATENT DOCUMENTS

EP 0 535 974 4/1993

(Continued)

*Primary Examiner*—Julian W. Woo
(74) *Attorney, Agent, or Firm*—Ryan Kromholz & Manion, S.C.

(57) ABSTRACT

A first surgical instrument has a bore extending therethrough and includes a handle attachment site. A second surgical instrument is sized and configured for passage through the bore of the first instrument. The handle is adapted for manipulating the first instrument when in use and includes a component configured to removably engage the handle attachment site. The handle includes a passageway accommodating passage of the second instrument through the bore of the first instrument while the first instrument is removably engaged by the handle.

8 Claims, 17 Drawing Sheets

U.S. PATENT DOCUMENTS

| | | | |
|---|---|---|---|
| 5,575,794 A | 11/1996 | Walus et al. | |
| 5,762,639 A | 6/1998 | Gibbs | |
| 5,772,678 A | 6/1998 | Thomason et al. | |
| 5,807,275 A | 9/1998 | Jamshidi | |
| 5,810,866 A | 9/1998 | Yoon | |
| 5,817,034 A * | 10/1998 | Milliman et al. | 600/566 |
| 5,910,197 A | 6/1999 | Chaconas | |
| 5,943,924 A | 8/1999 | Jarvis | |
| 6,165,137 A * | 12/2000 | Milliman et al. | 600/567 |
| D439,980 S | 4/2001 | Reiley et al. | |
| 6,221,029 B1 | 4/2001 | Mathis et al. | |
| D449,691 S | 10/2001 | Reiley et al. | |
| 6,468,279 B1 | 10/2002 | Reo | |

FOREIGN PATENT DOCUMENTS

| | | |
|---|---|---|
| EP | 0 591 851 | 4/1994 |
| GB | 2 243 788 | 11/1991 |
| WO | WO 99/37212 | 7/1999 |
| WO | WO 01/28439 | 4/2001 |

* cited by examiner

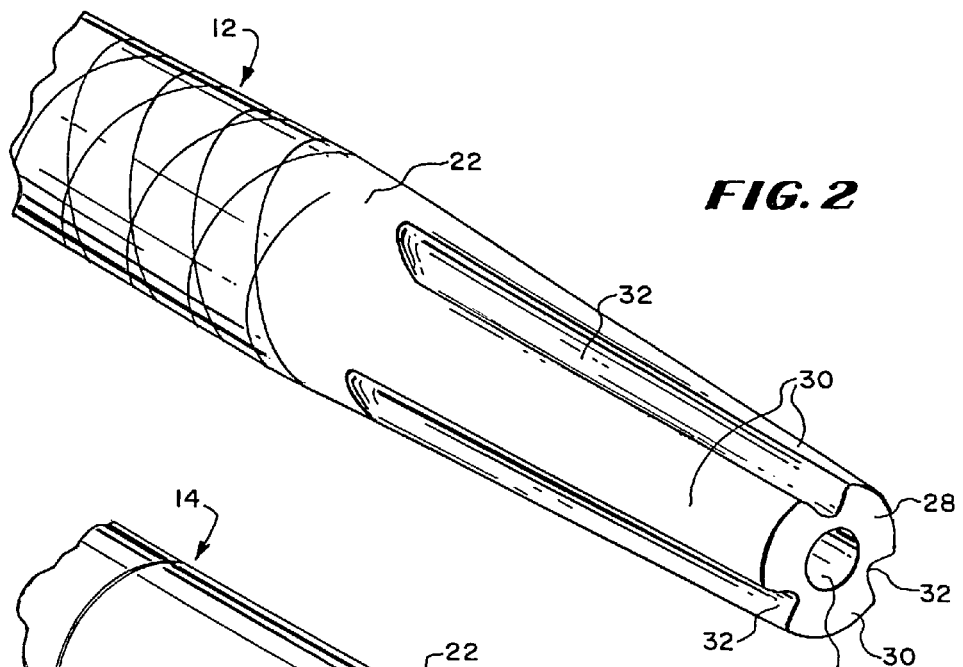
FIG. 2
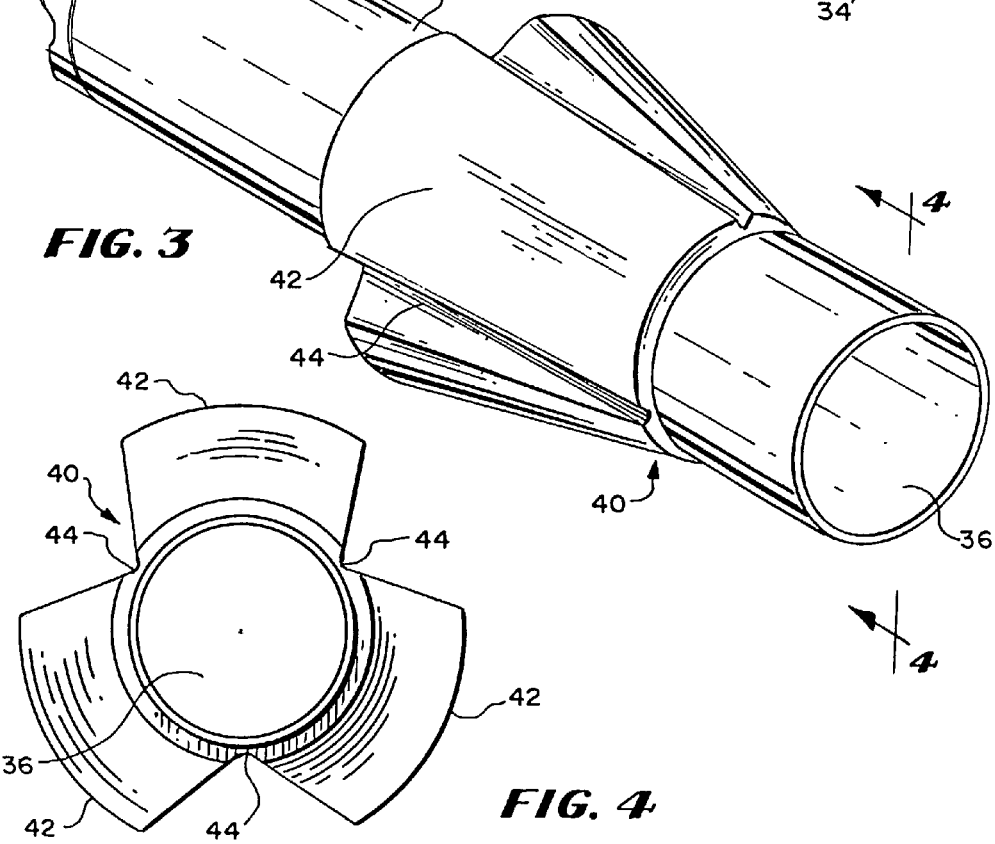
FIG. 3
FIG. 4

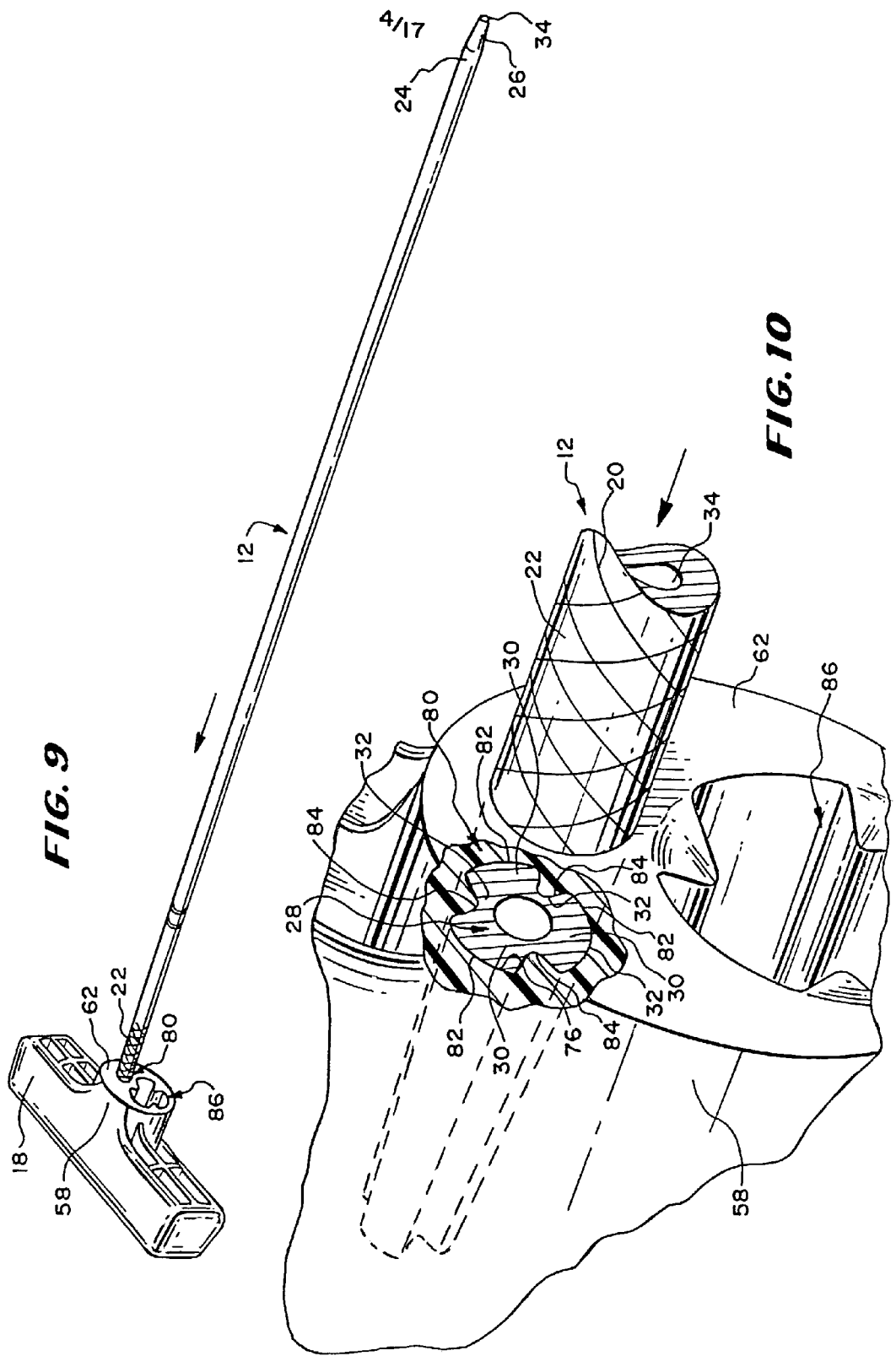

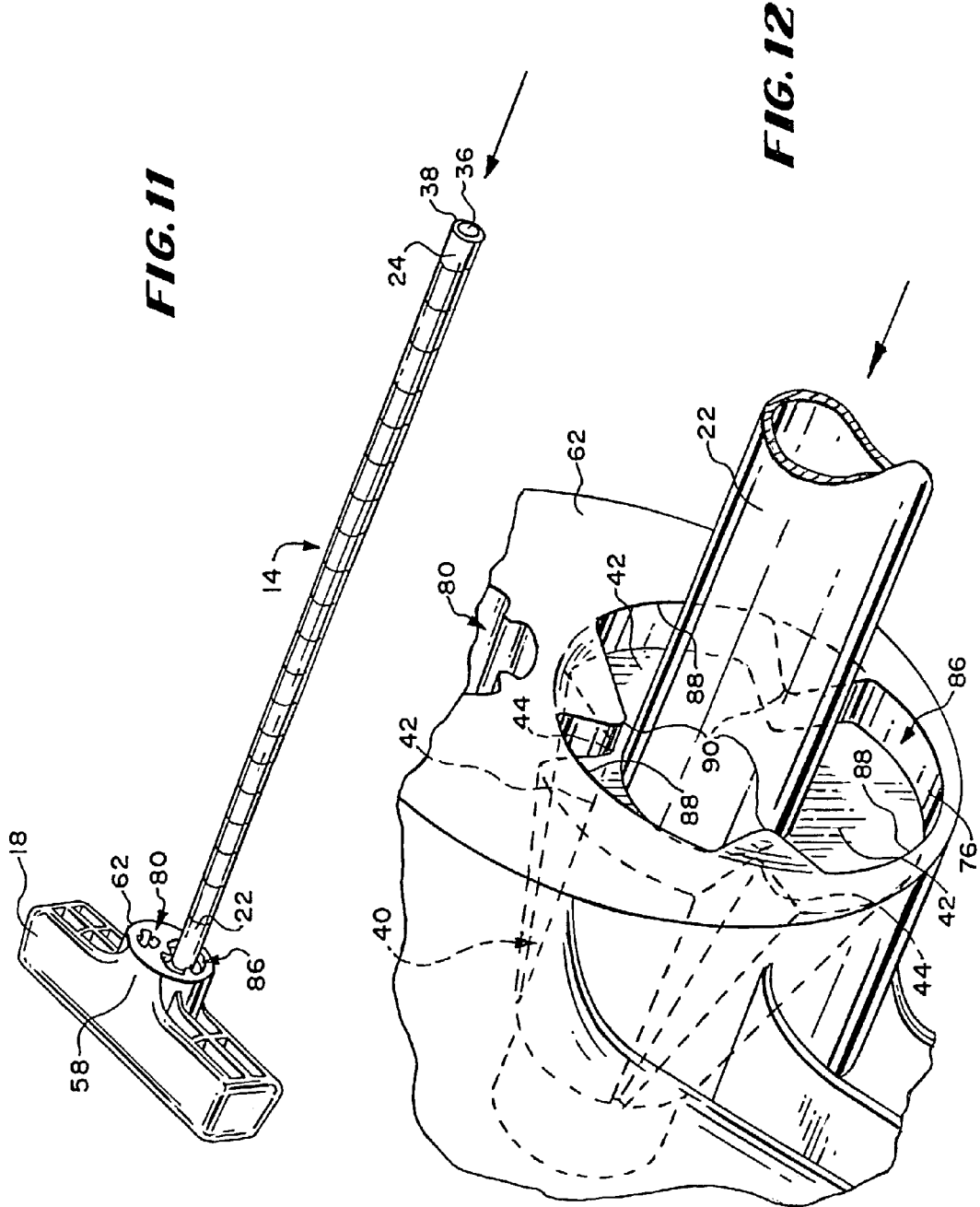

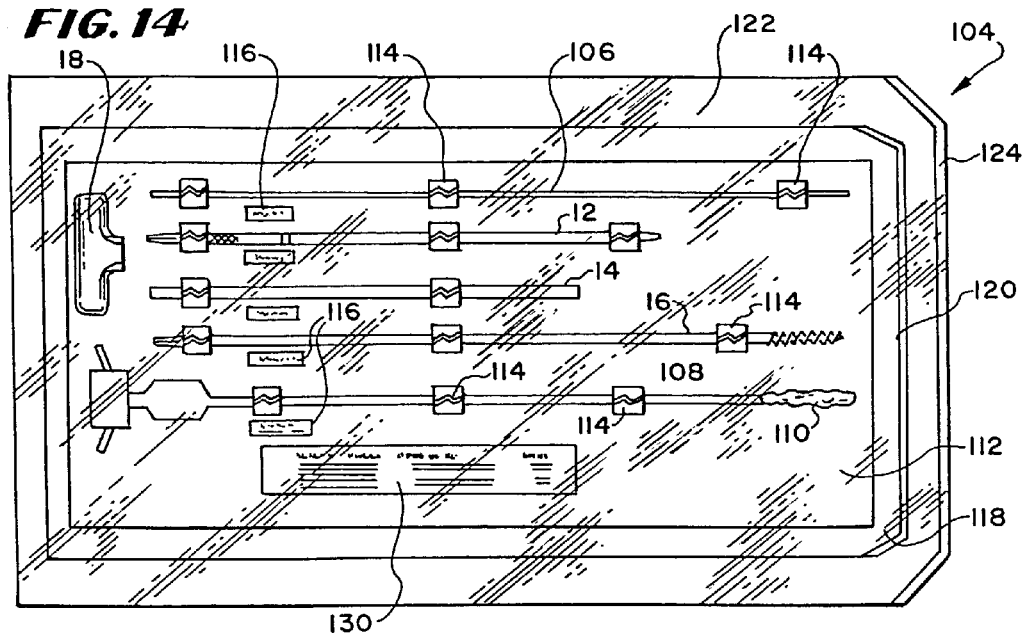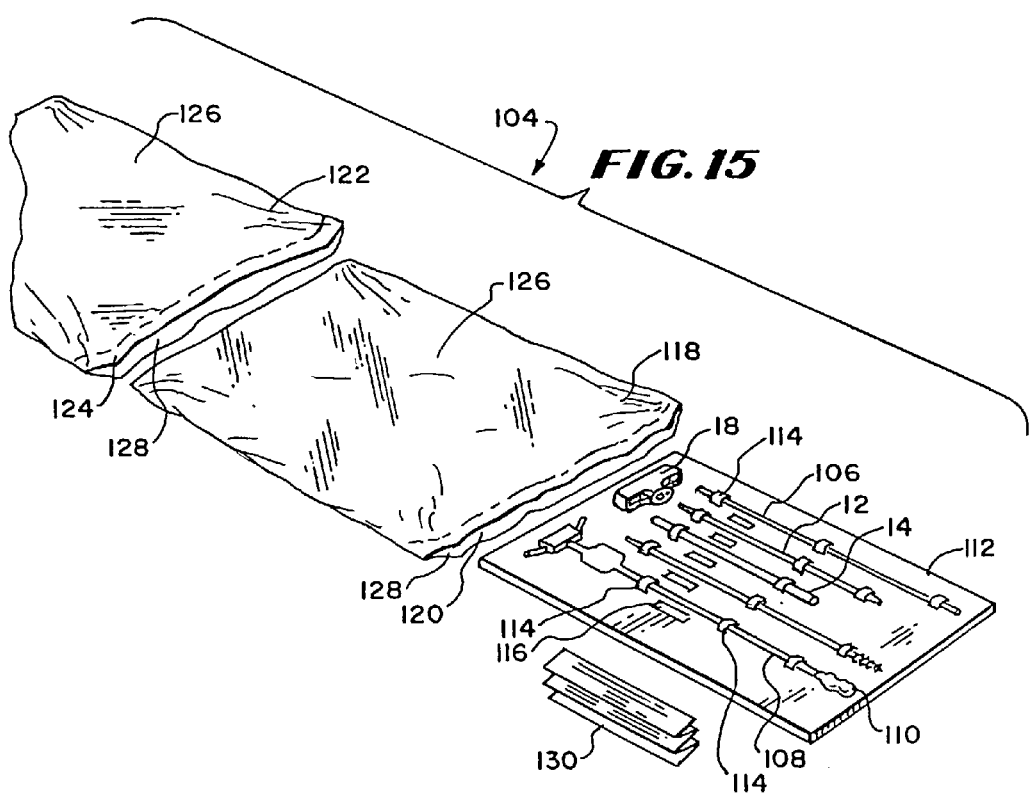

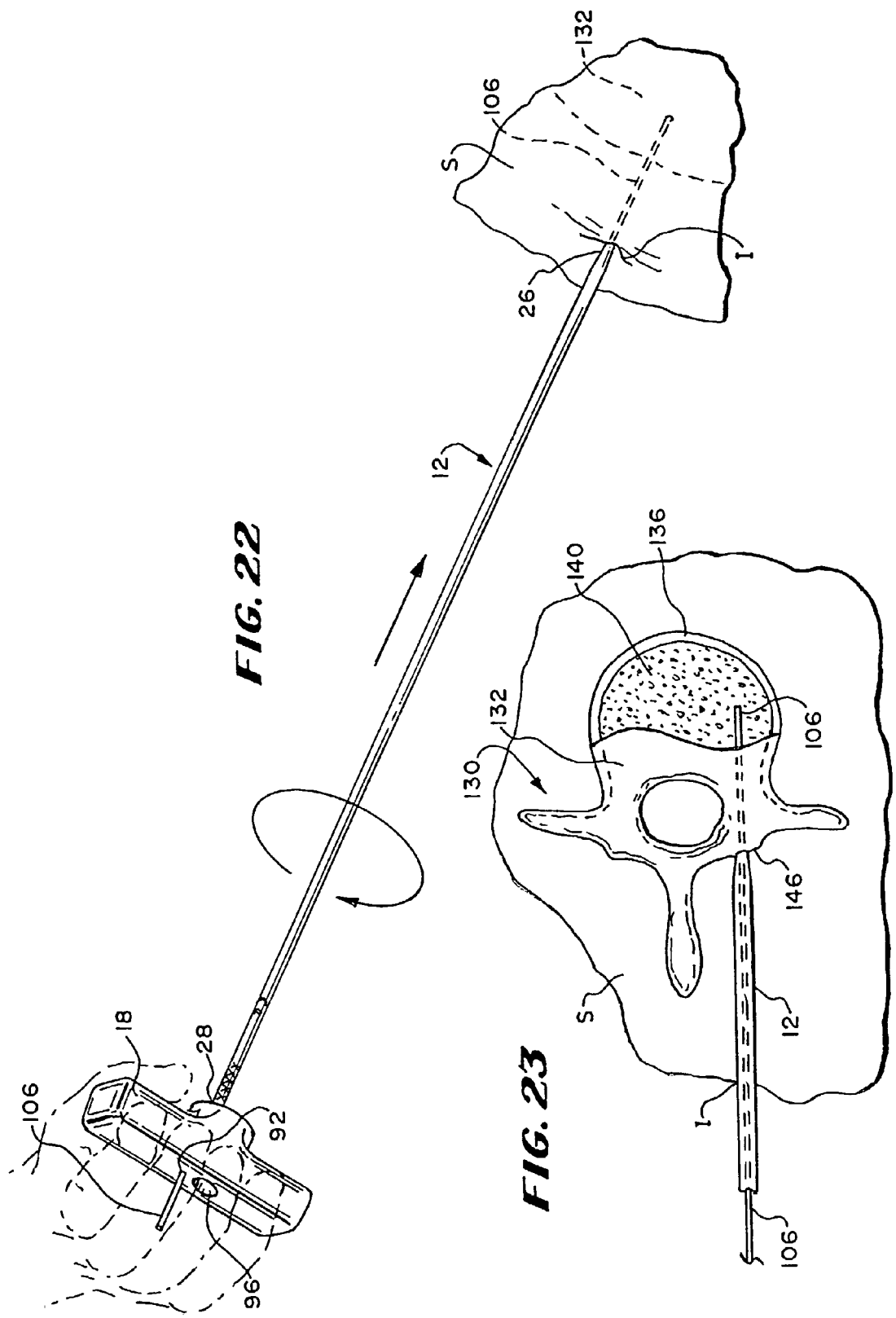

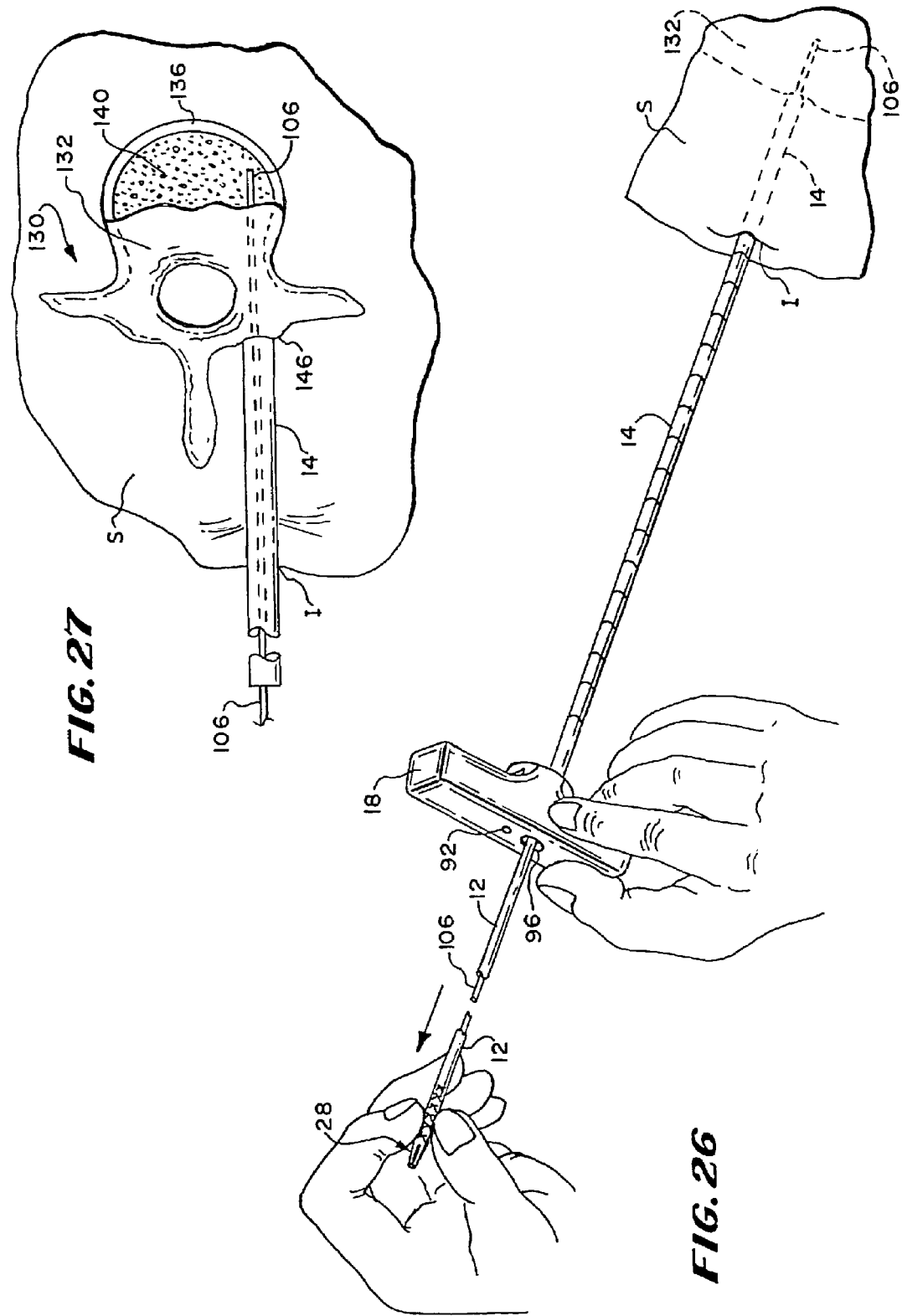

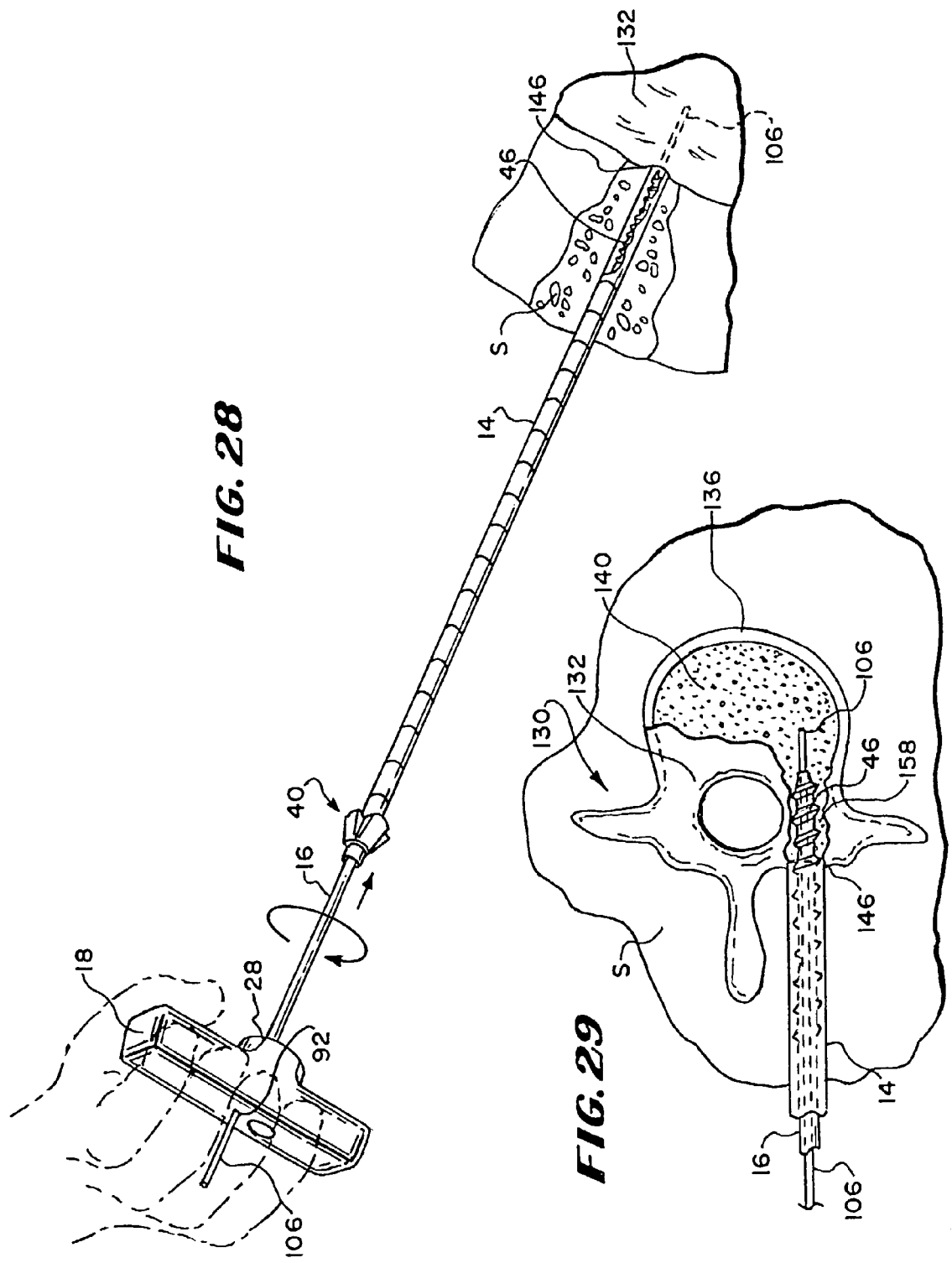

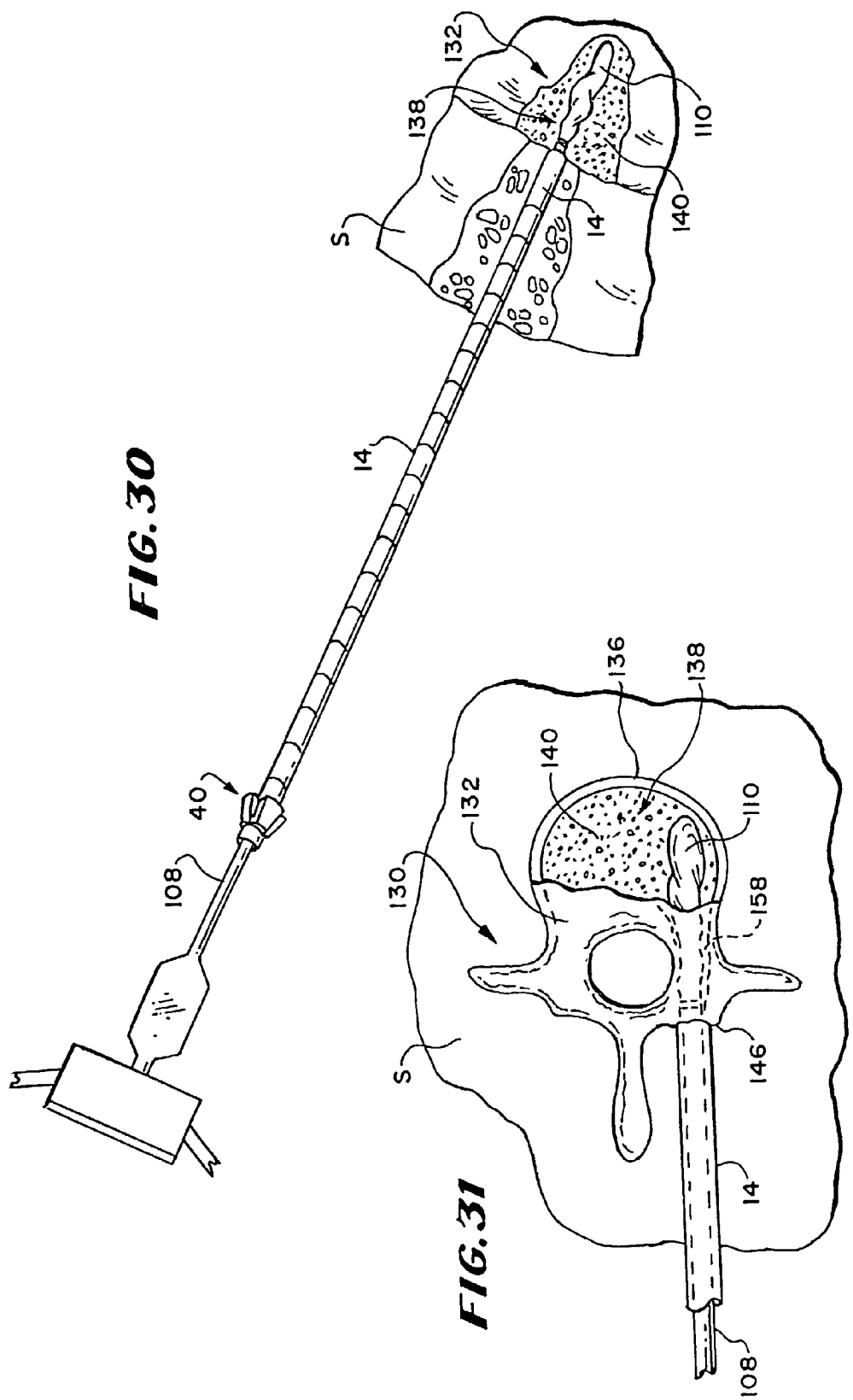

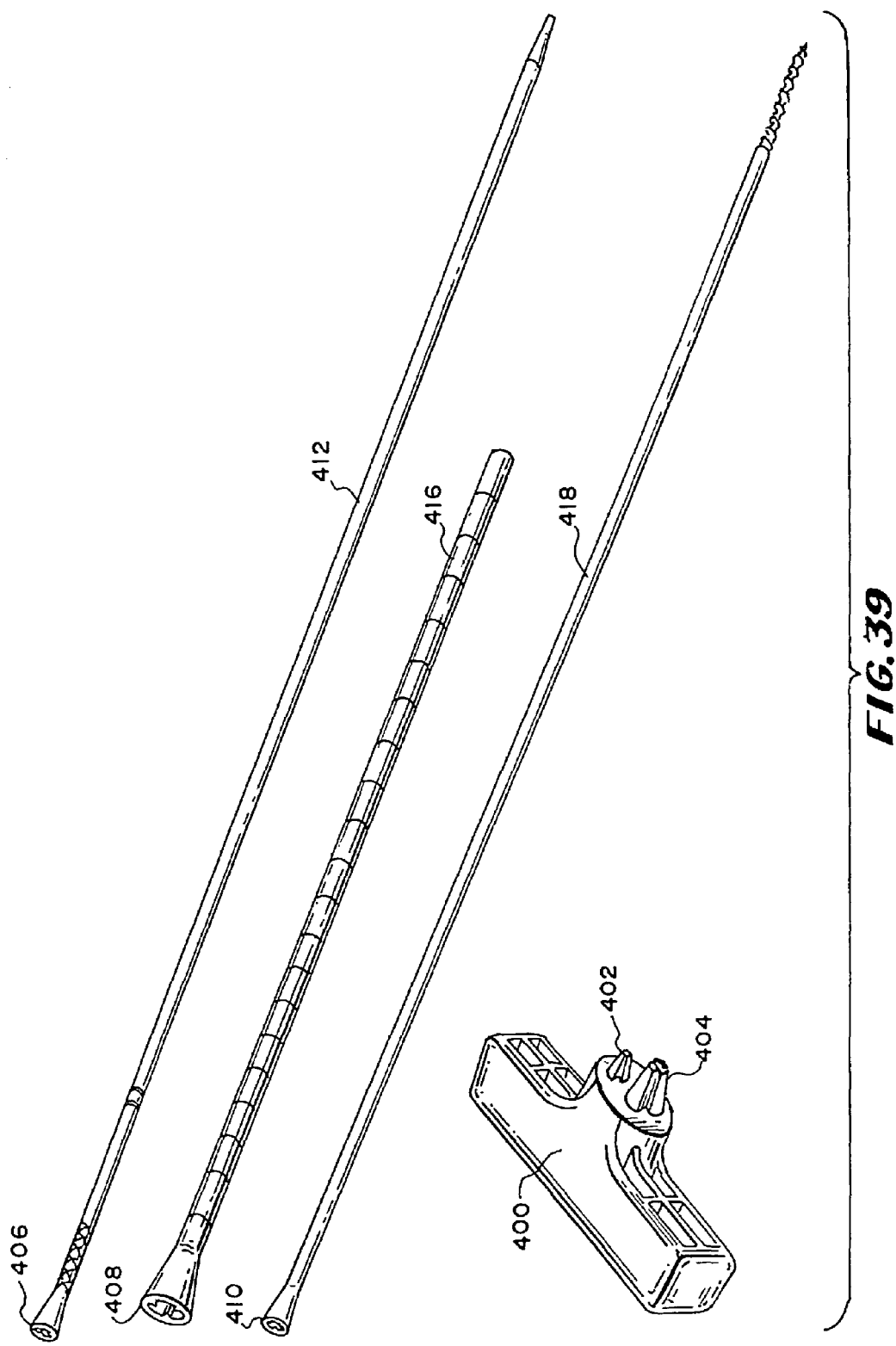

SLIP-FIT HANDLE FOR HAND-HELD INSTRUMENTS THAT ACCESS INTERIOR BODY REGIONS

RELATED APPLICATION

This application is a divisional of application Ser. No. 09/014,229, filed Jan. 27, 1998 now U.S. Pat. No. 6,468,279.

FIELD OF THE INVENTION

The invention generally relates to hand-held surgical instruments and to procedures that deploy these instruments through tissue to access interior regions of the body.

BACKGROUND OF THE INVENTION

There are many different types and styles of hand-held surgical instruments that physicians use to gain access into interior body regions. These instruments are intended to penetrate tissue by the application of pushing forces, twisting forces, or both in combination.

Often, a single surgical procedure will require the physician to employ different surgical instruments, each possessing a different shape, size, and function. Often, the procedure will require the physician to deploy these instruments in both soft and hard tissue to meet the diagnostic or therapeutic objectives of the procedure. The physician will often need an enhanced mechanical advantage to advance an instrument through tissue, particularly through dense or hard tissue, such as bone.

The common need to use different instruments in a given procedure, coupled with the absolute need to accurately and reliably deploy each of these different instruments through both soft and hard tissue, often with an enhanced mechanical advantage, complicate the physician's already difficult task. The need to handle different instruments in different ways for different purposes can distract the physician and lead to wasted effort, which lengthen the overall time of the procedure.

SUMMARY OF THE INVENTION

One aspect of the invention provides a surgical system comprising a cannula instrument, a guide pin instrument, and a handle. The cannula instrument has a bore extending therethrough and includes a handle attachment site. The guide pin instrument is sized and configured for passage through the bore of the cannula instrument. The handle is adapted for manipulating the cannula instrument when in use. The handle includes a component configured to removably engage the handle attachment site and further includes a passageway in the handle that accommodates passage of the guide pin instrument through the bore of the cannula instrument while the cannula instrument is removably engaged by the handle.

In one embodiment, the guide pin instrument includes a handle.

According to another aspect of the invention, the system further comprises a third functional instrument sized for passage through the bore of the cannula instrument after the guide pin instrument is removed from the bore of the cannula.

Features and advantages of the inventions are set forth in the following Description and Drawings, as well as in the appended claims.

BRIEF DESCRIPTION OF THE DRAWINGS

FIG. 2 is an enlarged perspective view of a first type of tapered flange, carried by at least one of the instruments shown in FIG. 1, which slip-fits into and out of the handle;

FIG. 3 is an enlarged perspective view of a second type of tapered flange, carried by at least one of the instruments shown in FIG. 1, which slip-fits into and out of the handle;

FIG. 4 an end view of the tapered flange shown in FIG. 3, taken generally along line 4—4 in FIG. 3;

FIG. 9 is a perspective view of an obturator instrument having a tapered flange of the type shown in FIG. 2 slip-fitted into the first socket of the handle shown in FIGS. 5 to 8, ready for use;

FIG. 10 is an enlarged perspective view, with portions broken away, showing the details of the slip fit engagement between the tapered flange and the first handle socket shown in FIG. 9;

FIG. 11 is a perspective view of a cannula instrument having a tapered flange of the type shown in FIGS. 3 and 4 slip-fitted into the second socket of the handle shown in FIGS. 5 to 8, ready for use;

FIG. 12 is an enlarged perspective view, with portions broken away, showing the details of the slip fit engagement between the tapered flange and the second handle socket shown in FIG. 11;

FIG. 14 is a top view of a kit for storing the one or more functional instruments in association with the handle shown in FIGS. 5 to 8 prior to use;

FIG. 15 is an exploded perspective view of the kit shown in FIG. 14;

FIG. 22 is a perspective view showing a subsequent step, after insertion of the guide pin component shown in FIGS. 19 to 21, which uses the handle shown in FIGS. 5 to 8 to aid in the deployment of an obturator instrument over the guide pin component;

FIG. 23 is a top view of the vertebral body, with the obturator instrument shown in FIG. 22 deployed;

FIG. 26 is a perspective view showing a subsequent step, after insertion of the cannula instrument shown in FIG. 24, which removes the obturator instrument from the cannula instrument, to leave the cannula instrument and guide pin component in place;

FIG. 27 is a top view of the vertebral body, after the obturator removal step shown in FIG. 26, leaving the cannula instrument and guide pin component in place;

FIG. 28 is a perspective view showing a subsequent step, after removal of the obturator instrument shown in FIG. 26, which uses the handle shown in FIGS. 5 to 8 to aid in the deployment of a drill bit instrument through the cannula instrument along the guide pin component;

FIG. 29 is a top view of the vertebral body, as the drill bit instrument shown in FIG. 28 is deployed with aid of the handle to open a passage into the interior volume of the vertebral body;

FIG. 30 is a perspective view showing a subsequent step, after removal of the drill bit instrument and guide pin component shown in FIG. 28, of deploying a catheter instrument carrying a diagnostic or therapeutic element through the cannula instrument into the vertebral body;

FIG. 31 is a top view of the vertebral body, as the diagnostic or therapeutic element carried by the catheter component shown in FIG. 30 is deployed into the interior volume of the vertebral body;

FIG. 39 is a perspective view of an alternative system including different functional instruments and a T-shaped handle that slip-fits into and out of engagement with the instruments, to aid a physician in manipulating the instruments during use.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

Figure 1:
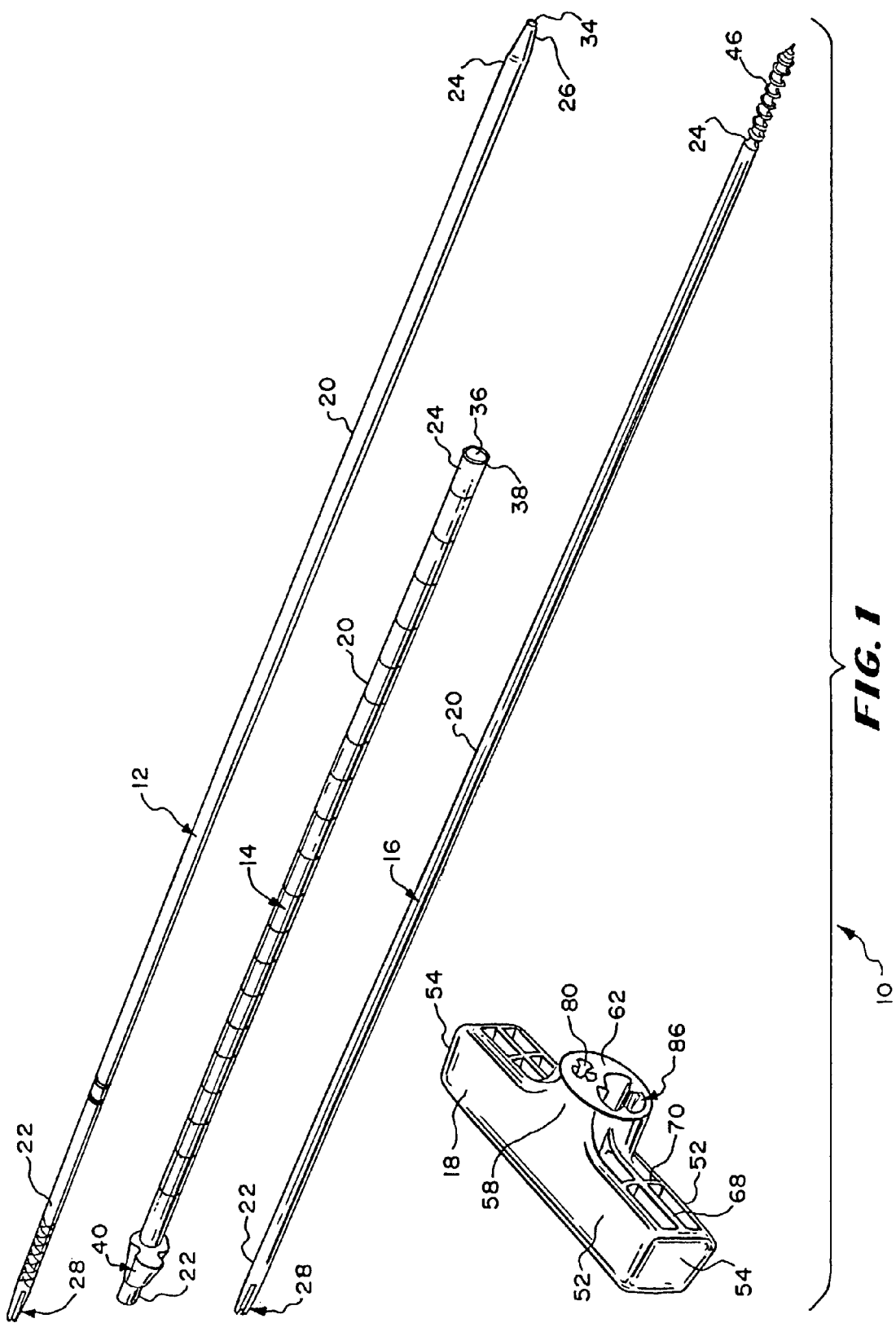
FIG. 1 is a perspective view of a system including different functional instruments and a T-shaped handle that slip-fits into and out of engagement with the instruments, to aid a physician in manipulating the instruments during use.

FIG. 1 shows a system 10 for penetrating tissue. The system includes one or more functional instruments 12, 14, and 16 and a handle 18. The handle 18 engages at least one of the functional instruments 12, 14, and 16 in a removable, slip fit fashion to aid a physician in manipulating the instrument 12, 14, or 16 during use.

I. The Instruments

The number and type of instruments 12, 14, and 16 can vary. FIG. 1 shows three representative instruments 12, 14, and 16, each having a different size and function.

The first, second, and third instruments 12, 14, and 16 share some common features, although they are intended, in use, to perform different functions. The first, second and third instrument 12, 14, and 16 each comprises an elongated, cylindrical body 20 having a proximal end 22 and a distal end 24. The first, second, and third instrument 12, 14, and 16 are each made of a rigid, surgical grade plastic or metal material.

A. The Obturator Instrument

The first instrument 12 functions as an obturator. Its distal end 24 is tapered to present a penetrating surface 26. In use, the surface 26 is intended to penetrate soft tissue in response to pushing or twisting forces applied by the physician at the proximal end 22.

The proximal end 22 of the obturator instrument 12 presents a flanged surface 28. As also shown in an enlarged view in FIG. 2, the flanged surface 28 tapers from a larger outer diameter to a smaller outer diameter in the direction of the proximal end 22. The flanged surface 28 includes an array of circumferentially spaced teeth 30 with intermediate flutes 32.

An interior lumen 34 extends through the obturator instrument 12 from the distal end 24 to the proximal end 22. The interior lumen 34 is sized to accommodate a conventional surgical guide pin component to aid in its deployment, as will be described in greater detail later.

B. The Cannula Instrument

The second instrument 14 functions as a cannula or guide sheath. The cannula instrument 14 is somewhat larger in diameter than and not as long as the obturator instrument 12. As shown in FIGS. 1 and 3, the cannula instrument 14 includes an interior lumen 36 that extends from its distal end 24 to its proximal end 22. The interior lumen 36 is sized to accept the obturator instrument 12. The size of the interior lumen 36 permits a physician to slide and rotate the cannula instrument 14 relative to the obturator instrument 12, and vice versa, as will be described in greater detail later.

The distal end 24 of the cannula instrument 14 presents an end surface 38. In use, the end surface 38 of the cannula instrument 14 is intended to penetrate soft tissue surrounding the obturator instrument 12, in response to pushing or twisting forces applied at the proximal end 22.

The proximal end 22 carries an enlarged fitting 40. As best shown in an enlarged view in FIGS. 3 and 4, the fitting 40 tapers from a larger diameter to a smaller diameter in the direction of the proximal end 22. Like the tapered flange 28 at the proximal end 22 of the obturator instrument 12, the tapered fitting 40 has an array of circumferentially spaced teeth 42 with intermediate flutes 44. The tapered fitting 40 of the cannula instrument 14 possesses a larger maximum outer diameter than the maximum outer diameter of the tapered flange 28 of the obturator instrument 12.

C. The Drill Bit Instrument

The third instrument 16 functions as a drill bit. The drill bit instrument 16 has generally the same physical dimensions as the obturator instrument 12. Like the obturator instrument 12, the drill bit instrument 16 is intended, in use, to fit for sliding and rotational movement within the interior lumen 36 of the cannula instrument 14.

The distal end 24 of the drill bit instrument 16 includes machined cutting edges 46. In use, the cutting edges 46 are intended to penetrate hard tissue in response to rotation and longitudinal load forces applied at the proximal end 22 of the drill bit instrument 16.

The proximal end 22 presents a tapered flange 28, substantially identical to the flange 28 on the obturator instrument 12, as FIG. 2 shows in an enlarged view. Like the obturator instrument 12, the tapered flange 28 changes from a larger diameter to a smaller diameter in the direction of the proximal end 22. The tapered flange 28 of the drill bit instrument 16 also includes an array of circumferentially spaced teeth 30 with intermediate flutes 32. The form and orientation of the teeth 30 and flutes 32 on the drill bit instrument 16 correspond to the form and orientation of the teeth 30 and flutes 32 on the obturator instrument 12.

II. The Handle

The handle 18 is made from a molded or cast rigid plastic or metal material. As also shown in FIGS. 5 to 8, the handle 18 is shaped to be comfortably and securely grasped by a normal human hand (see FIG. 8). The shape and size to accommodate this function can, of course, vary. In the embodiment shown in FIG. 5, the handle 18 is elongated along a main axis 48 to fit comfortably across the palm of the hand. In a representative embodiment, the handle 18 measures about 76 mm in length along the main axis 48, about 16 mm in width across the main axis 48, and about 25 mm in height normal to the main axis 48. These dimensions can, of course, vary to best serve the intended field of use.

Figure 8:
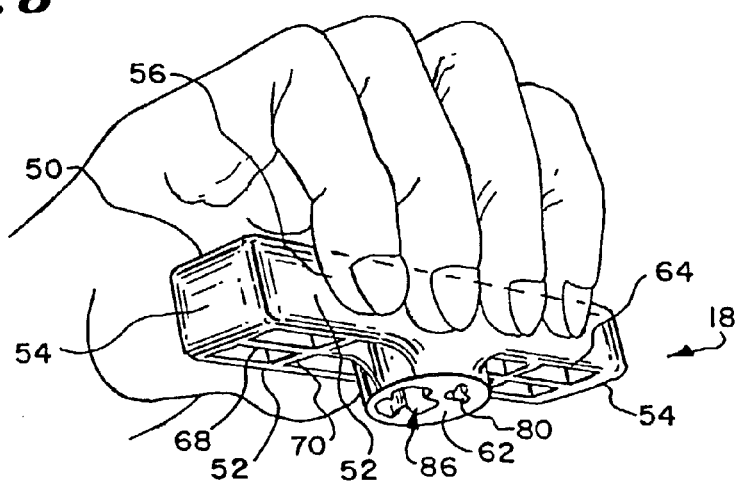
FIG. 8 is a side perspective view of the handle shown in FIG. 5, being grasped by a physician and ready for use.

The handle 18 includes a top wall 50, opposed side walls 52, and opposed end walls 54. The junctions 56 of the side walls 52 and end walls 54 with the top wall 50 are preferably rounded according to normal finger joint radii to provide a comfortable gripping area. The side walls 52 and end walls 54 also taper somewhat outward from the top wall 50 (see FIGS. 6 and 8), to enable firm, comfortable grasping between the fingers and thumb, as FIG. 8 shows. The top wall 50 and side walls 52 can be roughened or otherwise textured to provide a secure gripping surfaces. The contours of the handle 18 are also designed to minimize surgical glove tears.

Figure 6:
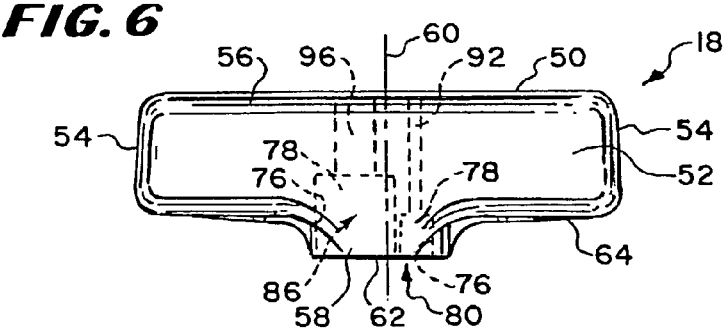
FIG. 6 is a side view of the T-shaped handle shown in FIG. 5.

The handle 18 includes a center post 58, which is integrally molded to the handle 18 about its geometric center 60 (as FIG. 6 shows). The center post 58 extends downward from the top wall 50 along the geometric center 60 between the side walls 52. The center post 58 has an exposed end surface 62, which terminates below the lower edges 64 of the side and end walls 52 and 54. This gives the handle 18 a general T-shape, when viewed from the side (see FIGS. 6 and 8).

Figure 7:
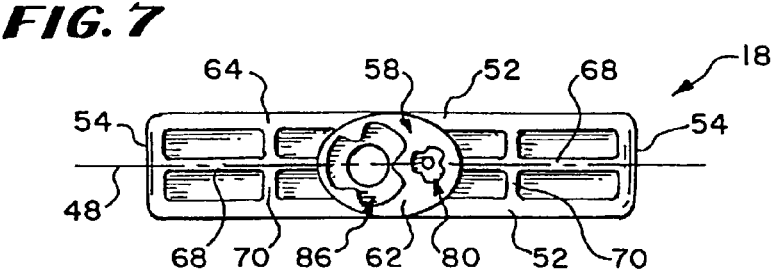
FIG. 7 is a bottom view of the T-shaped handle shown in FIG. 5, showing the first and second sockets of the handle.

The underside interior 66 of the handle 18 includes a crossing array of molded stiffening ribs 68 and 70 extending about the center post 58 (as best shown in FIG. 7). Long stiffening ribs 68 extend between the center post 58 and the end walls 54, along the main axis 48 of the handle 18. Cross ribs 70 extend across the long ribs 68 between the side walls 52. The ribs 68 and 70 provide the handle 18 with structural rigidity and strength to transmit, without failure, both longitudinal and torsional load forces.

The handle 18 includes at least one interior cavity or socket 80/86 in the center post 58. The socket 80/86 serves to guide the attachment between the handle 18 and at least one of the instruments 12, 14, and 16. Of course, the number of sockets 80/86 can vary. The illustrated embodiment shows two sockets 80 and 86. In this arrangement, each instrument 12, 14, and 16 in the system 10 can be fitted to the handle 18.

Both first and second sockets 80 and 86 open at the end surface 62 of the center post 58. Both sockets 80 and 86 (see FIG. 6) include interior side walls 76, which extend into the center post 58. Both sockets 80 and 86 include interior end walls 78 in the center post 58, spaced below the top wall 50 of the handle 18.

Referring to FIGS. 9 and 10, the interior side wall 76 of the first socket 80 includes an array of circumferentially spaced grooves 82 with intermediate splines 84. The form and orientation of the grooves 82 and splines 84 are sized to match the form and orientation of the teeth 30 and flutes 32 at the proximal ends 22 of the obturator instrument 12 and the drill bit instrument 16. The first socket 80 accepts the tapered flange 28 of either the obturator instrument 12 or the drill bit instrument 16. As FIG. 10 shows, the teeth 30 of the tapered flange 28 mesh in a slip-fit with the grooves 82 of the first socket 80. The running slip-fit allows longitudinal force to be applied to either instrument 12 or 16 through the handle 18. The running slip-fit also prevents relative rotation between either instrument 12 or 16 and the first socket 80, thereby permitting torsional or twisting forces to be applied to either instrument 12 or 16 by the handle 18, with an increased mechanical advantage.

Because of its larger size, the tapered fitting 40 of the cannula instrument 14 will not fit inside the first socket 80. Instead (see FIGS. 11 and 12), the interior side wall 76 of the second socket 86 is sized to accept the tapered fitting 40. The second socket 86 includes an array of circumferentially spaced grooves 88 with intermediate edges 90, which, in form and orientation, match the form and orientation of the teeth 42 and flutes 44 on the tapered fitting 40. The teeth 42 of the tapered fitting 40 mesh in a slip-fit with the grooves 88 of the second socket 86, as FIG. 12 shows. The running slip-fit allows both longitudinal and torsional forces to be applied to the cannula instrument 14 through the handle, with increased mechanical advantage.

Because of its smaller size, the tapered flange 28 of either the obturator instrument 12 or the drill bit instrument 16 will fit inside but not mesh with the second socket 86. The first and second sockets 80 and 86 thereby represent unique attachment sites for different functional instruments.

Figure 5:
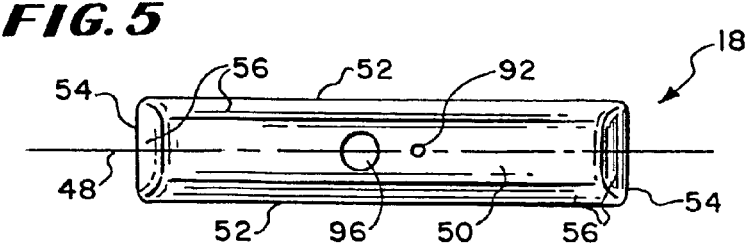
FIG. 5 is a top view of the T-shaped handle shown in FIG. 1.

Referring to FIGS. 5 and 6, a first passage 92 extends through the top wall 50 of the handle 18, through the center post 58, and into the first socket 80. The passage 92 is generally aligned with the center of the first socket 80 within the cavity 72. The first passage 92 is sized to pass a conventional surgical guide wire component through the handle 18 and into the lumen 34 of the obturator instrument 12, when fitted in the first socket 80. The interior side wall 76 of the first socket 80 is preferably tapered inward toward the first passage 92, to guide the guide wire through the socket 80 into the first passage 92 without sticking. This arrangement will be described in greater detail later.

Likewise, a second passage 96 extends through the top wall 50 of the handle 18, through the center post 58, and into the second socket 86. The passage 96 is generally aligned with the center of the second socket 86. The second passage 96 is sized to pass either the obturator instrument 12 or the drill bit instrument 16 through the handle 18 and into the lumen 36 of the cannula instrument 14, when fitted in the second socket 86. This arrangement will also be described in greater detail later.

III. The Form and Function of the Running Slip-Fit

The form and function of the running slip-fit between the teeth and flutes 30/32 or 42/44 on the selected instruments 12, 14, and 16 and the grooves and splines 82/84 in the corresponding sockets 80 and 86, allow the physician to fit the selected instrument 12, 14, or 16 to the handle 18 tactilely, without need of visual tracking or confirmation. At the same time, the form and function of the running slip-fit make possible the reliable transmission, with increased mechanical advantage, of both torsional and longitudinal loads by the handle 18 to the selected instrument 12, 14, or 16, without undue slippage or wasted motion. Furthermore, the form and function of the running slip-fit permit quick detachment of the selected instrument 12, 14, or 16 from the handle 18, without sticking or resort to inordinate force.

Figure 13:
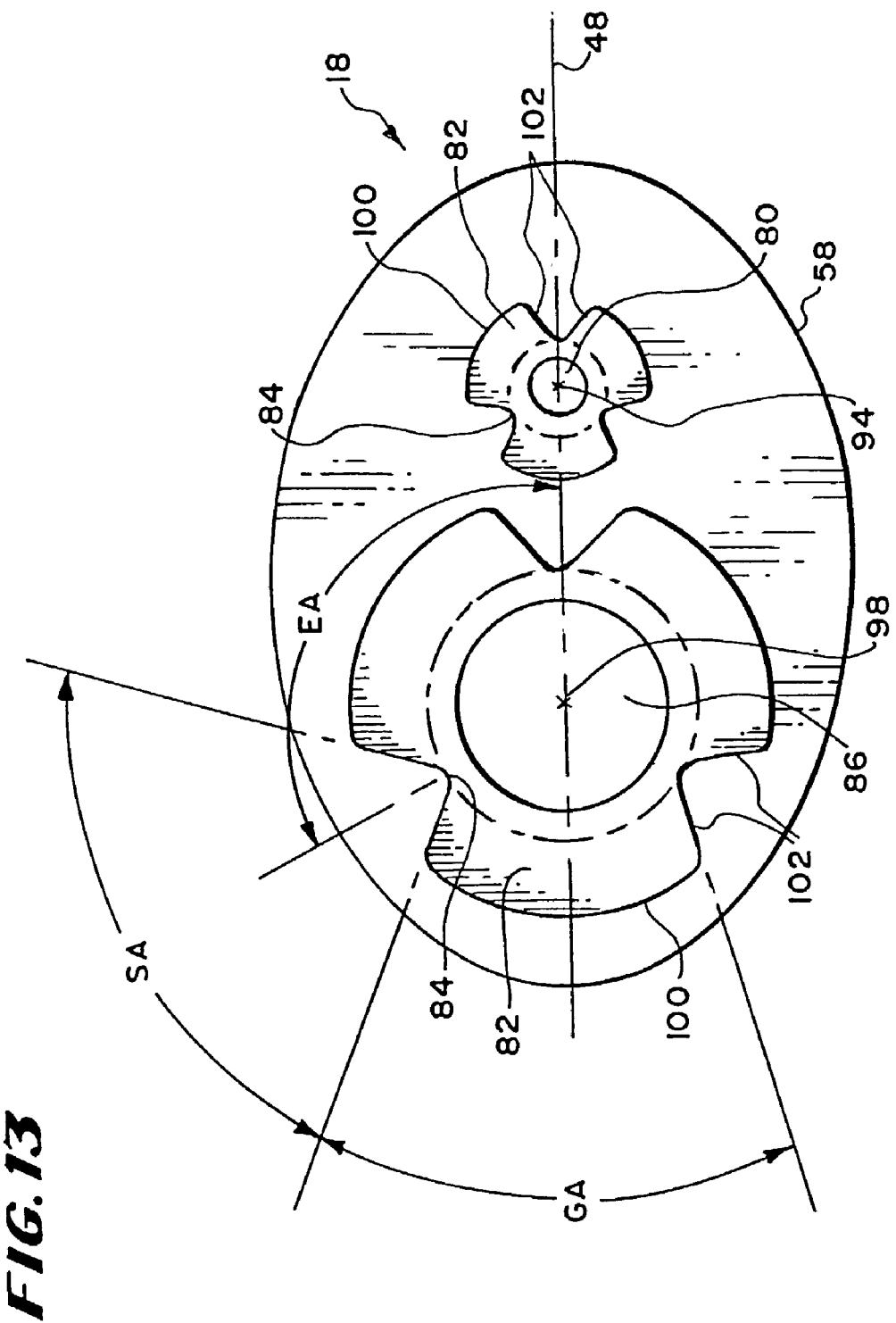
FIG. 13 is an enlarged view of the geometries of first and second sockets of the handle shown in FIGS. 5 to 8.

In the illustrated and preferred embodiment (see FIG. 13), the form and function of the sockets 80 and 86 are realized by use of three grooves 82 circumferentially spaced by intermediate splines 84. Each groove 82 comprises an arcuate section 100 that extends between two radial sections 102. Each spline 84 is defined between the radial sections 102 of two adjacent grooves 82.

The sockets 80 and 86 of the handle 18 can possess different sizes and arcuate relationships, smaller or larger, according to the intended use. For example, posterolateral access to a vertebral body is made using instruments having a larger dimension than instruments used to accomplish a transpedicular access. The sockets 80 and 86 on the handle 18 will therefore be sized differently, depending upon the dimensions of the mating instruments. Practicality and functionality dictate the minimum and maximum dimensions. The size and circumferential spacing of the sockets 80 and 86, as well as the overall dimensions of the handle 18 itself, are selected based upon desired performance, manufacturing, and ease of use criteria.

In an exemplary construction to be used with instruments for making a posterolateral access, in the first socket 80, the arcuate sections 100 of the grooves 82 lay at a diameter of about 5.2 mm and the splines 84 lay at a diameter of about 3.3 mm, measured from the center 94 of the first socket 80. In the second socket 86, the arcuate sections 100 of the grooves 82 lay along a diameter of about 12.8 mm and the splines 84 lay along a diameter of about 8.1 mm, measured from the center 98 of the second socket 86. In this exemplary embodiment, the first passage 92 has a diameter of about 1.8 mm, and the second passage 96 has a diameter of about 6.5 mm. In this exemplary embodiment, the center post 58 has a major diameter of about 22.8 mm and a minor diameter of about 15.8 mm. The center 94 of the first socket 80 is spaced inward along the main axis 48 from one side of the center post 58 by about 17 mm, while the center 98 of the second socket 86 is spaced inward along the main axis 48 from the same side by about 7.6 mm.

In an exemplary construction to be used with instruments for making a transpedicular access, in the first socket 80, the arcuate sections 100 of the grooves 82 lay at a diameter of about 3.0 mm and the splines 84 lay at a diameter of about 1.9 mm, measured from the center 94 of the first socket 80. In the second socket 86, the arcuate sections 100 of the grooves 82 lay along a diameter of about 7.4 mm and the splines 84 lay along a diameter of about 4.7 mm, measured from the center 98 of the second socket 86. In this exemplary embodiment, the first passage 92 has a diameter of about 1.0 mm, and the second passage 96 has a diameter of about 3.7 mm. In this exemplary embodiment, the center post 58 has a major diameter of about 22.8 mm and a minor diameter of about 15.8 mm. The center 94 of the first socket 80 is spaced inward along the main axis 48 from one side of the center post 58 by about 17.0 mm, while the center 98 of the second socket 86 is spaced inward along the main axis 48 from the same side by about 7.6 mm.

As shown, the arcuate section 100 of each groove 82 extends over an equal arc GA of about 30°, and the grooves 82 are equally spaced apart by an arc SA of about 90°. In this arrangement, the splines 84 are circumferentially spaced apart by an equal arc EA of about 120°.

In addition, in the illustrated embodiment, each spline 84 is rounded or filleted facing into the socket 80/86 to facilitate molding and manufacture. In an exemplary embodiment, the splines 84 in the first socket 80 are filleted at a radius of about 0.3 mm, and the splines 84 in the second socket 86 are filleted at a radius of about 0.6 mm.

The form and orientation of the teeth and flutes 30/32 and 42/44 on the mating instrument 12, 16, or 18 are selected to match the form and orientation of the grooves and splines 82/84 of the appropriate socket 80/86. The teeth and flutes 30/32 and 42/44 have as their respective maximum outer diameters a dimension that is about 12% less than the maximum interior diameter of the mating groove and spline 82/84, thereby providing a running slip fit, RC 8.

The form and function of the running slip-fit are also influenced by the relative size of the sockets 80/86. Tactile placement is enhanced by maximizing the difference in socket size, so that fitting the wrong instrument in the wrong socket is eliminated. This, in turn, dictates the design of the mating instruments 12, 14, and 16. The difference in socket sizes dictates the difference in sizes of the taper flanges 28 and fittings 40 on the various instruments 12, 14, and 16.

The form and function are also affected by the relative orientation of the first and second sockets 80/86 in the center post 58. In the illustrated and preferred embodiment, the first and second sockets 80 and 86 are placed in close side-by-side relationship along the main axis 48 of the handle 18. A groove 82 of the first socket 80 is oriented with a spline 84 of the second socket 86, or vice versa, to minimize the spacing between the two sockets 80 and 86, while maintaining structural integrity.

The close, side-by-side orientation of different size sockets 80 and 86, coupled with the form and orientation of each socket 80 and 86, allows for quick tactile recognition of the proper socket 80/86 on the handle 18 and quick tactile alignment of the mating tapered flanges 28 or tapered fittings 40 on the instrument 12, 14, and 16 in the identified socket 80 or 86. The filleted splines 84 allows for slip-fit engagement against the matching tapered flanges 28 or fittings 40 on the attached instrument 12, 14, or 16. The filleted splines 84 also allow ease of disengagement of the instrument 12, 14, and 16 from the handle 18, without sticking. The form and orientation of the tapered flanges 28 or fittings 40 also allow the application of torsional loads by the handle 18 about the axis of the attached instrument 12, 14, or 16, while the handle 18 applies a longitudinal load along the axis of the attached instrument 12, 14, or 16.

IV. Kit for Packaging the System

As shown in FIG. 14, a kit 104 is provided for storing the one or more functional instruments 12, 14, and 16 in association with the handle 18 prior to use. The kit 104 also includes other components 106 and 108, which are intended to be used in association with the instruments 12, 14, and 16 and handle 18. For example, the kit 104 shown in FIG. 14 includes a guide pin component 106 and a catheter component 108, which carries a diagnostic or therapeutic element 110 for deployment in the targeted interior body region.

Though not shown in FIG. 14, the kit 104 can also include a conventional spinal needle assembly 152, which will be described in greater detail later.

The kit 104 can take various forms. In the illustrated embodiment, the kit 104 comprises a sterile, wrapped assembly.

In this assembly (see FIG. 15 also), the kit 104 includes an interior tray 112 made, e.g., from die cut cardboard, plastic sheet, or thermo-formed plastic material. The tray 112 includes spaced apart tabs 114, which hold the handle 18, instruments 12, 14, and 16, and components 106 and 108 in a secure position during sterilization and storage prior to use.

Preferably, the tray 112 presents the handle 18, instruments 12, 14, and 16, and components 106 and 108 in an ordered, organized layout, which is arranged to aid the physician in carrying out the intended procedure. For example, the layout of the tray 112 can present the instruments 12, 14, and 16 and components 106 and 108 in top-to-bottom order, according to sequence of intended use. For example, in a typical bone access procedure (as will be demonstrated in greater detail later), the guide pin component 106 is deployed first, followed by the obturator instrument 12, then the cannula instrument 14, then the drill bit instrument 16, and lastly the catheter component 108. Accordingly, the tray 112 packages these instruments and components in a top-to-bottom order, with the guide pin component 106 topmost, the obturator instrument 12 next, the cannula instrument 14 next, the drill bit instrument 16 next, and the catheter component lowermost 108. When a spinal needle assembly 152 is included in the kit 104, the spinal needle assembly 152 is mounted above the guide pin component 106.

In this layout, the handle 18 is packaged to the side of the instruments 12, 14, and 16. The tray 112 can include written labels 116 identifying the handle 18 and each instrument and component contained in the kit 104.

When packaged as a sterile assembly, the kit 104 includes an inner wrap 118, which is peripherally sealed by heat or the like, to enclose the tray 112 from contact with the outside environment. One end of the inner wrap includes a conventional peal-away seal 120, to provide quick access to the tray 112 at the instant of use, which preferably occurs in a sterile environment, such as within an operating room.

When packaged as a sterile assembly, the kit 104 also includes an outer wrap 122, which is also peripherally sealed by heat or the like, to enclosed the inner wrap. One end of the outer wrap 122 includes a conventional peal-away seal 124, to provide access to the inner wrap 118 and its contents. The outer wrap 122 can be removed from the inner wrap 118 in anticipation of imminent use, without compromising sterility of the handle 18, instruments 12, 14, and 16, and components 106 and 108 themselves.

Each inner and outer wrap 118 and 122 includes a peripherally sealed top sheet 126 and bottom sheet 128 (see FIG. 15). In the illustrated embodiment, the top sheet 126 is made of transparent plastic film, like polyethylene or MYLAR™ material, to allow visual identification of the contents of the kit 104. The bottom sheet 128 is made from a material that is permeable to ETO sterilization gas, e.g., TYVEK™ plastic material (available from DuPont).

The kit 104 also preferably includes in the tray 112 directions 130 for using the handle 18, the instruments 12, 14, and 16, and the components 106 and 108 to carry out a desired procedure. An exemplary procedure which the directions can describe will be explained later.

When packaged as a sterile assembly, the directions 130 can include the statement "For Single Patient Use Only" (or comparable language) to affirmatively caution against reuse of the contents of the kit 104. The directions 130 also preferably affirmatively instruct against resterilization of the handle 18, instruments 12, 14, and 16, or components 106 and 108 and also instructs the physician or user to dispose of the entire contents of the kit 104 upon use in accordance with applicable biological waste procedures.

The presence of the handle 18, instruments 12, 14, and 16, and components 106 and 108 packaged in the sterile kit 104 verifies to the physician or user that the contents are sterile and have not been subjected to prior use. The physician or user is thereby assured that the handle 18, instruments 12, 14, and 16, and components 106 and 108 meet established performance and sterility specifications.

It should be appreciated that the instruments and components contained in the kit 104 can be packaged into several, smaller functional kits. For example, a tool kit can package a spinal needle assembly, a guide pin component, an obturator instrument, a cannula instrument, and a drill bit instrument, together with the handle. A separate catheter kit can package the catheter component. Another separate cement kit can package a cement nozzle and tamp. FIGS. 14 and 15 illustrate one of many different possible embodiments.

V. Illustrative Use of the System

The following describes use of the handle 18, instruments 12, 14, and 16, and components 106 and 108 shown in FIG. 14 packaged in the kit 104 in the context of treating bones. This is because these items can be advantageously used for this purpose. Still, it should be appreciated that the handle 18 is not limited to use in the treatment of bones. The handle 18 can be used in association with virtually any hand-held instrument intended to contact tissue to perform a diagnostic or therapeutic function.

The handle 18, instruments 12, 14, and 16, and components 106 and 108 will described with regard to the treatment of human vertebra. It should be appreciated, however, their use is not limited to human vertebrae. The handle 18 can be used in association with hand-held instruments in the treatment of diverse human or animal bone types.

Figure 16:
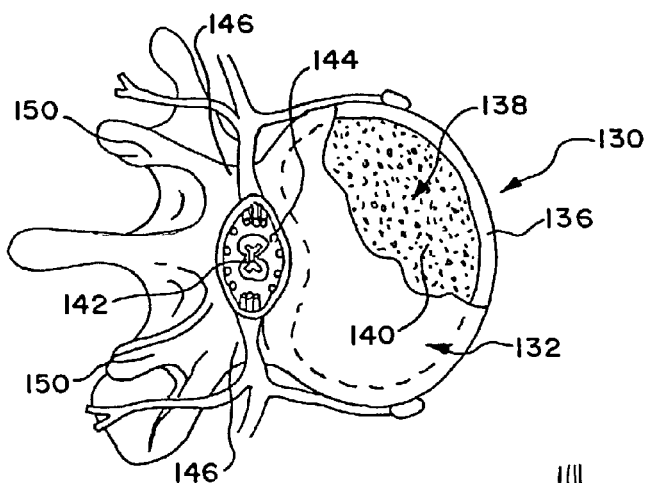
FIGS. 16 and 17 are, respectively, top and side views of a human vertebral body.
Figure 17:
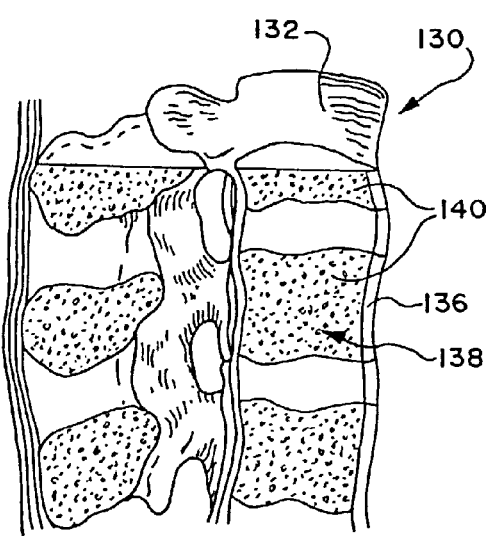

A typical vertebra 130 (see FIGS. 16 and 17) includes a vertebral body 132, which extends on the anterior (i.e., front or chest) side of the vertebra 130. The vertebral body 132 has the shape of an oval disk. The vertebral body 132 includes an exterior formed from compact cortical bone 136. The cortical bone 136 encloses an interior volume 138 of reticulated cancellous, or spongy, bone 140 (also called medullary bone or trabecular bone).

The spinal cord 142 passes through the spinal canal of the vertebra 132. The vertebral arch 144 surrounds the spinal canal 142. The pedicles 146 of the vertebral arch adjoin the vertebral body 134. The spinous process 148 extends from the posterior of the vertebral arch 144, as do the left and right transverse processes 150.

Figure 18:
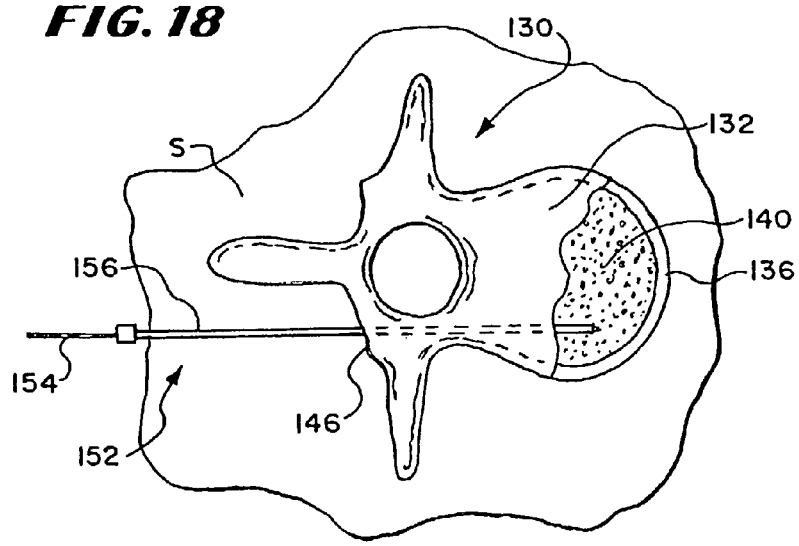
FIG. 18 is a top view of a vertebral body during insertion of a spinal needle assembly to begin a bone access procedure.

Referring first to FIG. 18, in a typical procedure, a patient lies on an operating table, while the physician introduces a conventional spinal needle assembly 152 into soft tissue (designated S in the drawings) in the patient's back. The patient can lie facedown on the table, or on either side, or at an oblique angle, depending upon the physician's preference. Indeed, the procedure can be performed through an open anterior procedure or an endoscopic anterior procedure.

The spinal needle assembly 152 comprises a stylet 154 slidably housed within a stylus 156. The assembly 152 typically has, for example, about an 18 gauge diameter. Other gauge diameters can and will be used to accommodate appropriate guide pins.

Under radiologic or CT monitoring, the physician advances the assembly 152 through soft tissue S down to and into the targeted vertebra 132, as FIG. 18 shows. The physician will typically administer a local anesthetic, for example, lidocaine, through assembly 152. In some cases, the physician may prefer other forms of anesthesia.

The physician directs the spinal needle assembly 152 to penetrate the cortical bone 136 and the cancellous bone 140 of the targeted vertebra 132. Preferably the depth of penetration is about 60% to 95% of the vertebral body 134.

FIG. 18 shows gaining access to cancellous bone 140 through the pedicle 146, which is called transpedicular access. However, posterolateral access, through the side of the vertebral body 134 may be indicated, based upon the objectives of the treatment or for other reasons based upon the preference of the physician.

Figure 19:
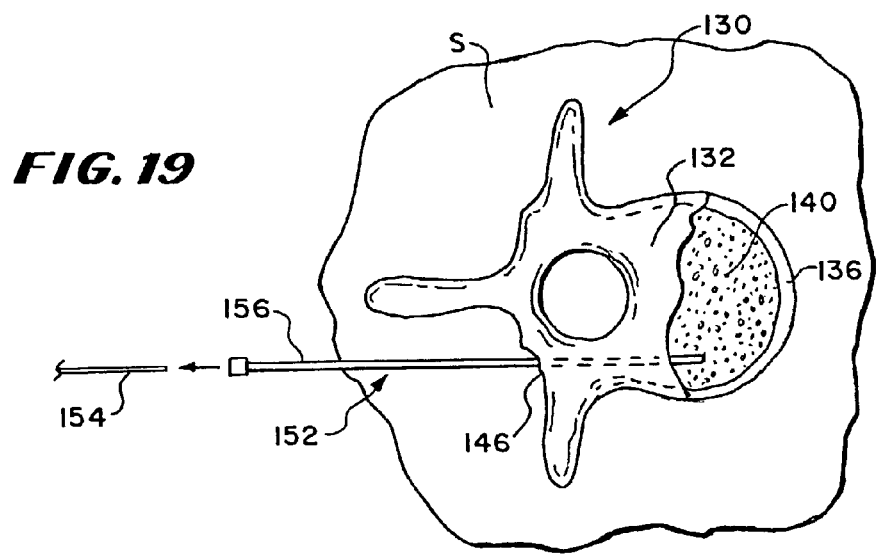
FIGS. 19 to 21 are top views showing subsequent steps, after insertion of the spinal needle assembly shown in FIG. 18, of inserting a guide pin component into the vertebral body.

Referring now to FIG. 19, after positioning the spinal needle assembly 152 in cancellous bone, the physician holds the stylus 156 and withdraws the stylet 154. It is at this time, or slightly before, that the outer and inner wraps 118 and 122 of the kit 104 can be removed, exposing the components carried on the tray 112 for use.

Figure 20:
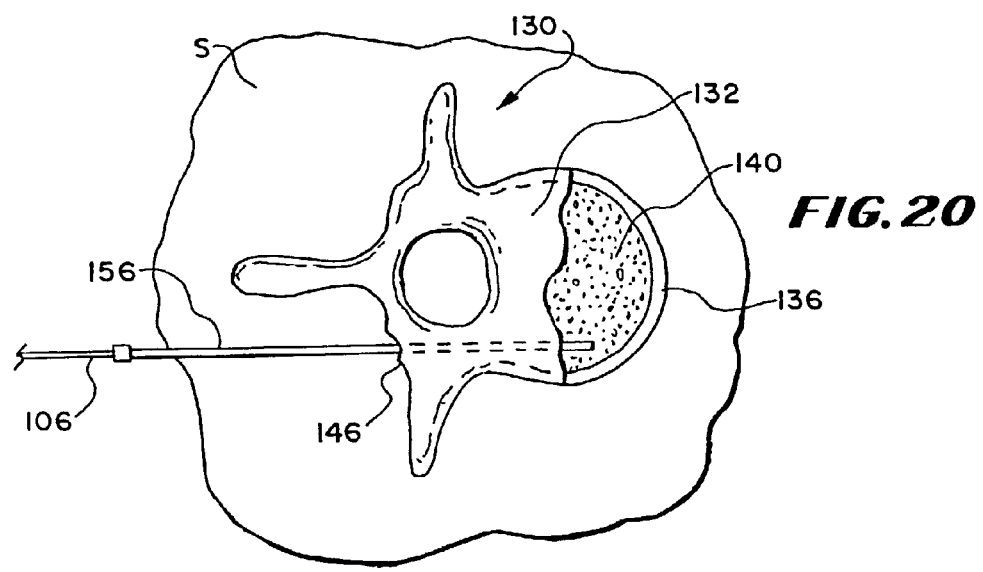
Figure 21:
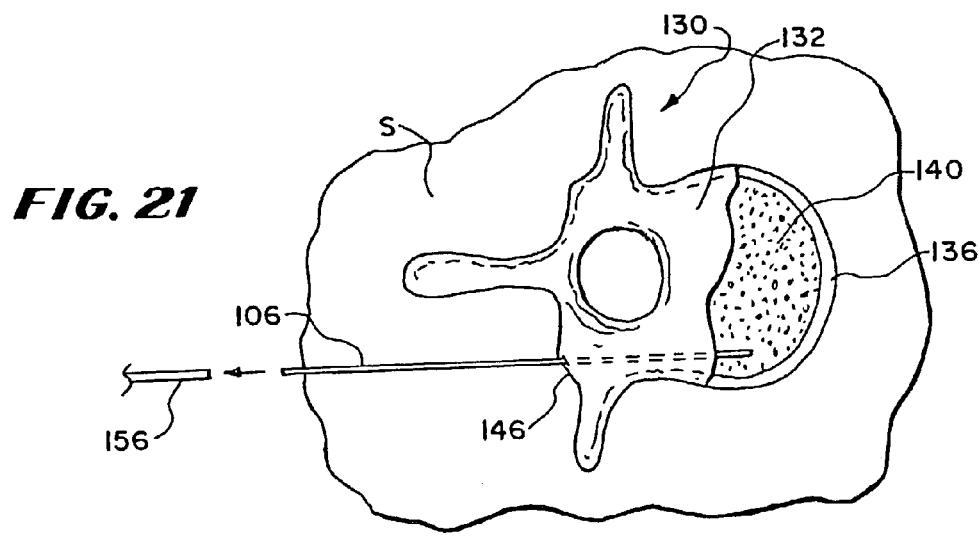

The physician first acquires the guide pin component 106 from the tray 112. As FIG. 20 shows, while still holding the stylus 156, the physician slides the guide pin component 106 through the stylus 156 and into the cancellous bone 140. As FIG. 21 shows, the physician now removes the stylus 156, leaving the guide pin component 106 deployed within the cancellous bone 140.

The physician next acquires the obturator instrument 12 and the handle 18 from the tray 112. As FIG. 22 shows, the physician slides the obturator instrument 12 over the guide pin component 106, distal end first. The physician slides the guide pin component 106 through the first passage 92 and the first socket 80 of the handle 18. As previously described, the interior side wall 76 of the first socket 80 is preferably tapered inward to guide the guide wire into the first passage 92 without sticking. The physician slides the handle 18 along the guide pin component 106 toward the tapered flange 28 of the obturator instrument 12, until achieving a running slip-fit between the first socket 80 and the tapered flange 28, in the manner previously described. The obturator instrument 12 is now ready for use.

As FIG. 22 shows, the physician makes a small incision (designated I in FIG. 22) in the patient's back. The physician twists the handle 18 while applying longitudinal force to the handle 18. In response, the tapered surface 26 of the obturator instrument 12 rotates and penetrates soft tissue through the incision I. The physician may also gently tap the handle 18, or otherwise apply appropriate additional longitudinal force to the handle 18, to advance the obturator instrument 12 through the soft tissue S along the guide pin component 106 down to the entry pedicle 146. The physician can also tap the handle 18 with an appropriate striking tool to advance the sharpened surface 26 of the obturator instrument 12 into the pedicle 146 to secure its position, as FIG. 23 shows.

The physician next slides the handle 18 along the guide pin component 106 away from the obturator instrument 12 to disengage the tapered flange 28 from the first socket 80. The physician then proceeds to slide the handle 18 completely off the guide pin component 106. The physician acquires the cannula instrument 14 from the tray 112.

Figures 24, 25:
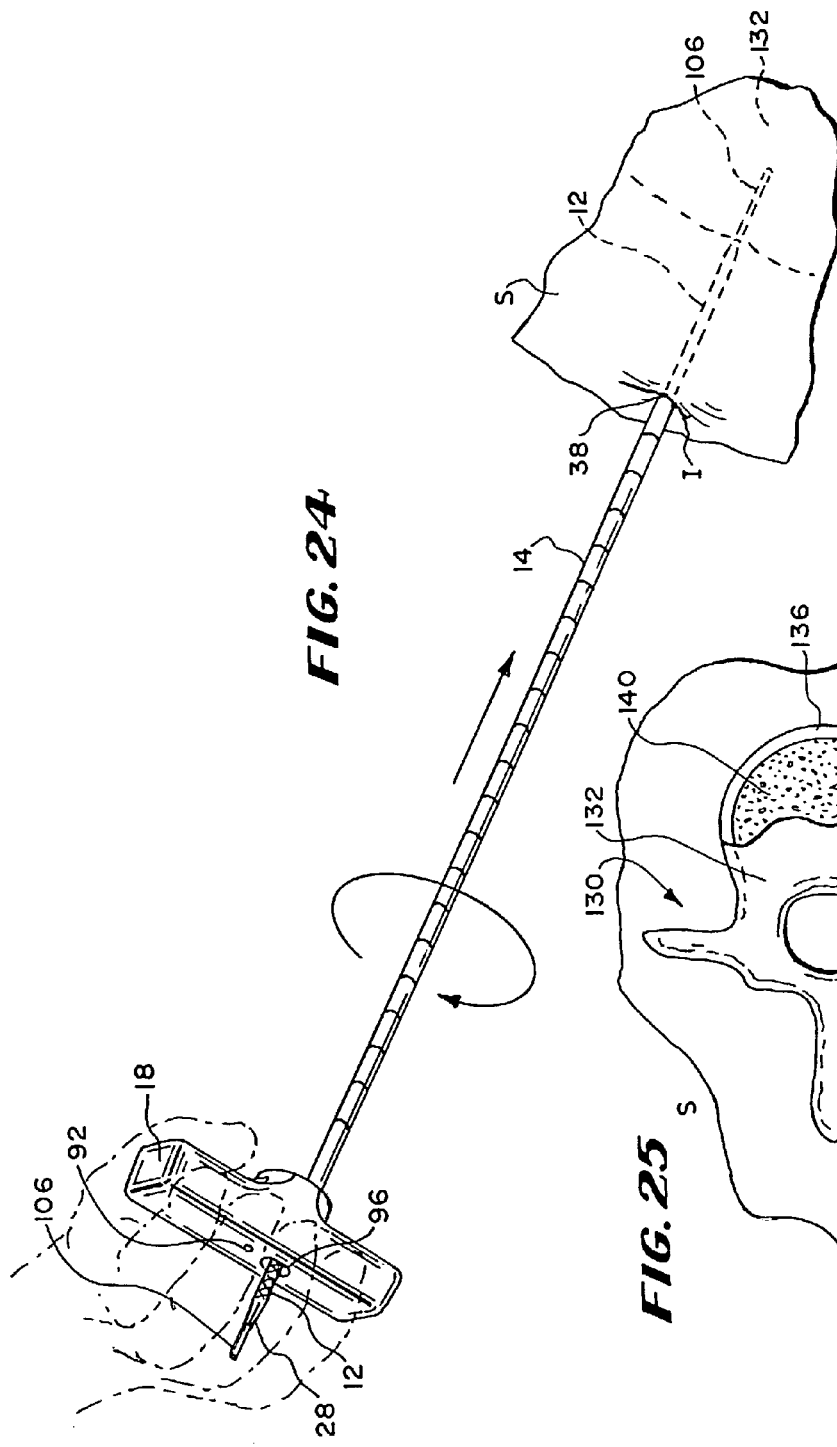
FIG. 24 is a perspective view showing a subsequent step, after insertion of the obturator instrument shown in FIG. 22, which uses the handle shown in FIGS. 5 to 8 to aid in the deployment of a cannula instrument over the obturator instrument.
FIG. 25 is a top view of the vertebral body, with the cannula instrument shown in FIG. 24 deployed.

As FIG. 24 shows, the physician slides the cannula instrument 14 over the guide pin component 106, distal end first, and, further, over the obturator instrument 12, until contact between the end surface 38 and tissue occurs. The physician now slides the guide pin component 106 through the second passage 96 and second socket 86 of the handle 18. The physician slides the handle 18 toward the tapered fitting 40 of the cannula instrument 14 until a running slip-fit occurs between the second socket 86 and the tapered fitting 40, as previously described. The cannula instrument 14 is now ready for use.

As Fig. F shows, the physician applies appropriate twisting and longitudinal forces to the handle 18, to rotate and advance the cannula instrument 14 through soft tissue along the obturator instrument 12. As FIG. 25 shows, when the end surface 38 of the cannula instrument 14 contacts cortical bone 136, the physician appropriately taps the handle with a striking tool to advance the end surface 38 into the pedicle 146 to secure its position.

As FIG. 26 shows, the physician now withdraws the obturator instrument 12, sliding it off the guide pin component 106, to leave the guide pin component 106 and the cannula instrument 14 in place, as FIG. 27 shows. The physician slides the handle 18 along the guide pin component 106 away from the cannula instrument 14 to disengage the tapered fitting 40 from the second socket 86. The physician then slides the handle 18 completely off the guide pin component 106. The physician now acquires the drill bit instrument 16 from the tray 112.

The physician slides the drill bit instrument 16 over the guide pin component 106, distal end first, through the cannula instrument 14 until contact with the bone tissue occurs. The physician next leads the guide pin component 106 through the first passage 92 and first socket 80 of the handle 18. As previously described, the preferred taper of the first socket 80 guides the guide wire through the socket 80 into the first passage 92 without sticking. As FIG. 28 shows, the physician slides the handle 18 along the guide pin component 106 toward the tapered flange 28 of the drill bit instrument 16, until a running slip-fit occurs between the first socket 80 and the tapered flange 28, as previously described. The drill bit instrument 16 is now ready for use.

As FIG. 29 shows, under X-ray control (or using another external visualizing system), the physician applies appropriate twisting and longitudinal forces to the handle 18, to rotate and advance the cutting edge 46 of the drill bit instrument 16 to open a passage 158 through the bone tissue and completely into the cancellous bone 140. The drilled passage 158 preferable extends no more than 95% across the vertebral body 134.

The physician now slides the handle 18 along the guide pin component 106 away from the drill bit instrument 16 to disengage the tapered flange 28 from the first socket 80. The physician, further, slides the handle 18 completely off the guide pin component 106.

The physician can now remove the drill bit instrument 16 and the guide pin component 106, leaving only the cannula instrument 14 in place, as FIGS. 30 and 31 show. The passage 158 made by the drill bit instrument 16 remains. Access to the cancellous bone 140 has been accomplished.

The physician can now acquire the catheter component 108 from the tray 112. The physician can advance a diagnostic or therapeutic element 110 carried by the catheter component 108 through the cannula instrument 14 and passage 158 into the interior volume 138 of the vertebral body 134.

The diagnostic or therapeutic element 110 of the catheter component 108 can be configured to perform various functions. For example, the distal element 110 can comprise a biopsy instrument, to obtain samples of cancellous bone. Alternatively, the distal element 110 can be a stylet to introduce a medication or the like into cancellous bone. Still alternatively (as shown in the illustrated embodiment), the distal element 110 can comprise an expandable body to compact cancellous bone 140 and form a cavity in the vertebral body 134, in the manner disclosed in U.S. Pat. Nos. 4,969,888 and 5,108,404, which are incorporated herein by reference. Upon compaction of cancellous bone, the distal element 110 can also include a nozzle to inject a flowable bone cement material into the formed cavity.

VI. Alternative Handle Configurations

As before explained, the shape of the handle 18 can vary. FIGS. 5 to 8 show a handle 18 with a generally T-shaped configuration.

A. Round Handle

Figure 32:
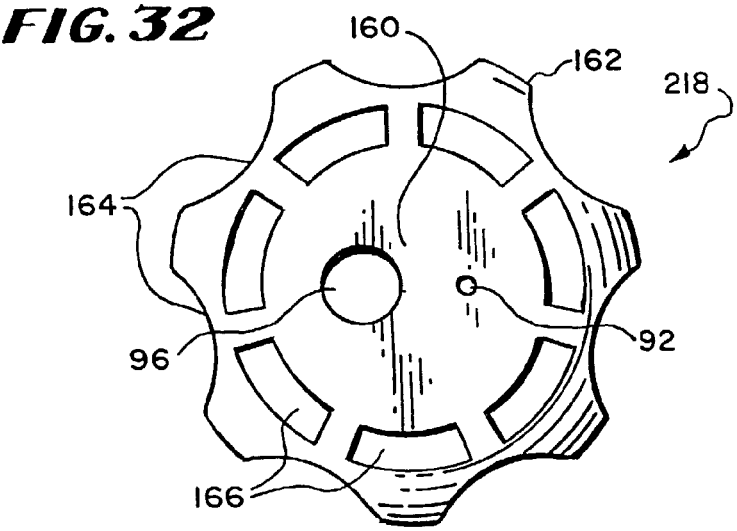
FIG. 32 is a top view of a round handle, which can be used in association with the functional instruments shown in FIG. 1, in generally the same fashion as the T-shaped handle shown in FIGS. 5 to 8.
Figure 33:
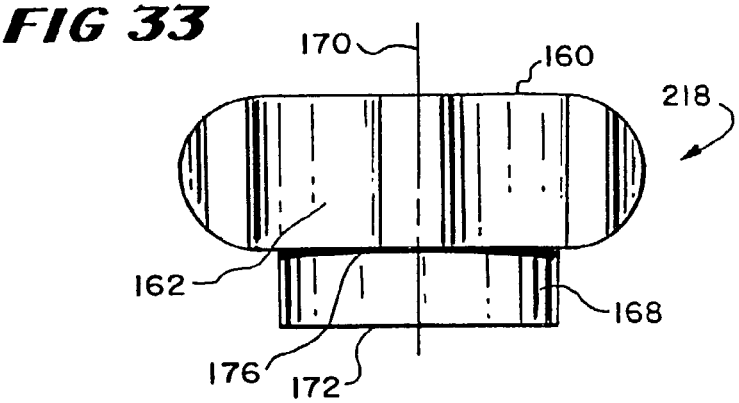
FIG. 33 is a side view of the round handle shown in FIG. 32.
Figure 34:
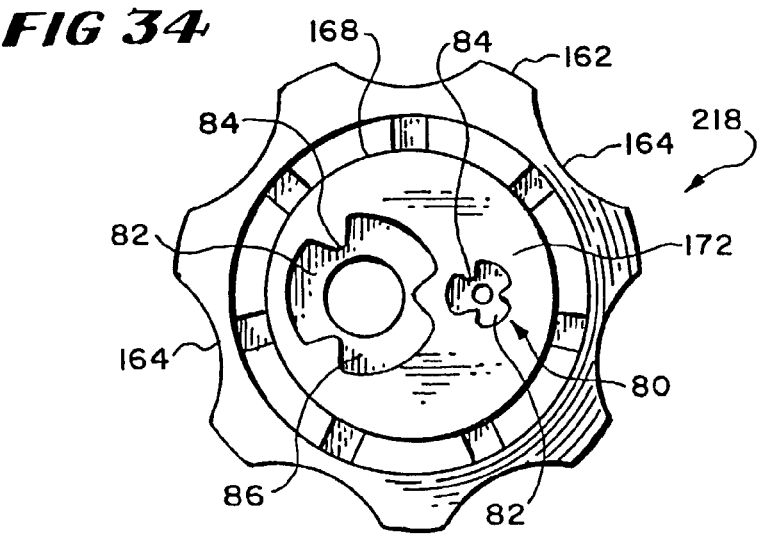
FIG. 34 is a bottom view of the round handle shown in FIG. 32, showing the first and second sockets of the handle.

FIGS. 32 to 34 show a representative alternative embodiment, in which a handle 218 has a general round configuration, made from a molded rigid plastic or metal material. The round handle 218 is also shaped to be comfortably and securely grasped by a normal human hand. In a representative embodiment, the handle 218 measures about 38 mm in diameter.

The handle 218 includes a top wall 160 and a peripheral side wall 162. The junction of the side wall 162 with the top wall 160 is preferably rounded to provide a comfortable grip. In addition, the side wall 162 includes a series of circumferentially spaced scallops 164 to assist the transmission of turning forces. In the illustrated embodiment, seven equally spaced scallops 164 are present to provide an appropriate turning resolution. The scallops 164 are each curved inwardly to comfortable accommodate the dimension of a thumb (e.g., with a radius of curvature of about 9 mm to 10 mm). The top wall 160 and the side wall 162 can be roughened or otherwise textured to enhance the over grip.

In the illustrated embodiment, the top wall 160 includes circumferentially spaced voids 166 aligned with each scallop 164. The voids 166 reduce the overall weight of the handle 218 and are arranged to provide optimal balance for the handle 218.

Like the T-shaped handle 18, the round handle 218 includes a center post 168, which is integrally molded to the walls 160 and 162 about the geometric center 170 of the handle 218. The center post 168 extends downward from the top wall 160 along the geometric center 170 between the side wall 162. The center post has an exposed end surface 172, which terminates below the lower edge 176 of the side wall 162. In an exemplary embodiment, the center post 168 has an outside diameter of about 22.8 mm, which is about the same outside diameter as the center post 58 of the T-shaped handle 18.

The round handle 218 likewise includes the first and second sockets 80 and 86 to enable attachment of the various instruments, in the same manner as previously described. The sockets 80 and 86 include arrays of grooves 82 circumferentially spaced by splines 84. The form, orientation, and size of the grooves 82 and splines 84 can be same as already described and shown in FIG. 13 to match the form and orientation of the teeth and flutes 30/32 and 42/44 at the proximal ends of the obturator instrument 12 and the drill bit instrument 14 (in the first socket 80) and the cannula instrument 12 (in the second socket 86). The tapered flanges 28 and fitting 40 thereby mesh in a running slip-fit in the appropriate first and second sockets 80 and 86.

As explained with respect to the T-shaped handle 18, the comparable running slip-fit that the round handle 218 provides, allows both longitudinal and twisting forces to be applied to the attached instrument 12, 14, and 16 through the handle 218. The different sizes of the first and second sockets 80 and 86 on the round handle 218 likewise represent the same sort of unique attachment sites for the different functional instruments, as previously explained for the T-shaped handle 18.

Like the T-shaped handle 18, first and second passages 92 and 96 extend through the top wall 160 of the round handle 218 and into the first and second sockets 80 and 86, respectively. The first passage 92 is sized to pass a conventional surgical guide wire through the handle 218 and into the lumen of the obturator instrument 12 or drill bit instrument 165 fitted in the first socket 80. The second passage 96 is sized to pass either the obturator instrument 12 or the drill bit instrument 16 through the handle 218 and through the lumen 36 of the cannula instrument 14 fitted in the second socket 86.

B. Anvil Handle

FIGS. 35 to 38 show another alternative embodiment of a handle 318, which embodies features of the invention. In this embodiment, the handle 318 is characterized by an elliptical "anvil" shape.

Figure 35:
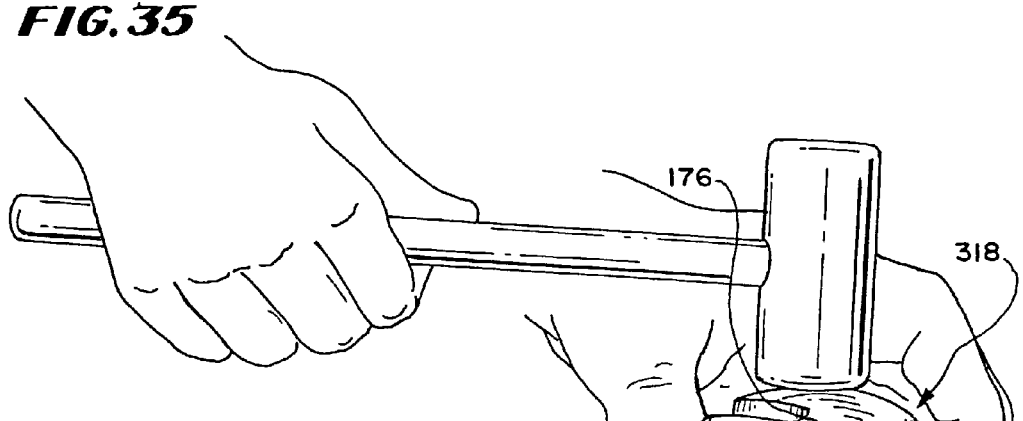
FIG. 35 is a perspective view of an elliptical, anvil-style handle, which can be used in association with the functional instruments shown in FIG. 1 when greater tapping or compression force is required to advance an instrument, particularly through hard tissue, like bone.

The elliptical handle 318 has a top wall 176 and a side wall 178 made from a molded rigid plastic or metal material. The handle 318 is dimensioned to be grasped between the forefinger and the thumb, with the top wall 176 facing upward, as FIG. 35 shows. The shape and orientation, when held by the physician, are intended to facilitate the application of greater tapping or striking forces, to advance an attached instrument 12/14/16 through denser or harder tissue, such as skeleton bone.

In an exemplary embodiment, the top wall 176 has a length dimension along it major axis 180 of about 57.2 mm and a length dimension along its minor axis 182 of about 50.8 mm. In the exemplary embodiment, the side wall 178 extends below the top wall 176 for a distance of about 11.3 mm.

The side wall 178 is chamfered inward, to present concave front and rear gripping surfaces 184 and 186, which are spaced apart along the major axis 180. In the illustrated embodiment, the radius of chamfer for the front surface 184 is intended to match the joint radius of the forefinger. The radius of the chamfer for the rear surface 186 is intended to match the joint radius of the thumb. Preferably, both the forward and rearward surfaces 184 and 186 are knurled or roughed to enhance the physician's grip.

As FIG. 35 shows, the inward chamfer of the side wall 178 shelters the physicians's hand from the top wall 176, on which the striking forces are applied. The top wall 176 is also preferably bowed upward, to present a raised striking surface, which further distances the physician's hand from the point of impact of the striking instrument.

A portion of the rear gripping surface 186 is cut away to form two interior sockets 188 and 190. The sockets 188 and 190 are axially oriented. The second socket 190 possesses an interior dimension, which is larger than the interior dimension of the first socket 188.

The form and size of the first interior dimension of the first socket 188 is intended to receive the proximal end 22 of either the obturator instrument 12 or the drill bit instrument 16, but not the cannula instrument 14, in a releasable interference snap-fit. In this arrangement, the proximal end of the instrument 12 and 16 can include a tapered flange 28, as already described, but need not. The releasable snap-fit stabilizes the instrument 12 or 16 in the first socket 188 for the application of a striking force on the top wall 176.

In like fashion, the form and size of the second interior dimension of the second socket 190 is intended to receive the proximal end 22 of the cannula instrument 14, but not the obturator instrument 12 or the drill bit instrument 16, in a releasable interference snap-fit. In this arrangement, the proximal end 22 of the cannula instrument 14 can include a tapered fitting 40, as already described, but need not. The releasable snap-fit stabilizes the cannula instrument 14 in the second socket 190 for the application of a striking force on the top wall 176.

Since the first and second sockets 188 and 190 extend through the handle 318, the handle 318 will accommodate the passage of a guide pin component 106 and the like through any instrument attached to the handle 318. For the same reason, the handle 318 will also accommodate the passage of smaller diameter instrument within a larger diameter instrument held by the handle 318.

The form and orientation of the sockets 188 and 190 in the elliptical handle 318 also permit the physician, using only tactile sensing, to insert the selected instrument into the desired socket 188 or 190 and remove the attached instrument from the socket 188 or 190, without need of visual intervention.

Figure 36:
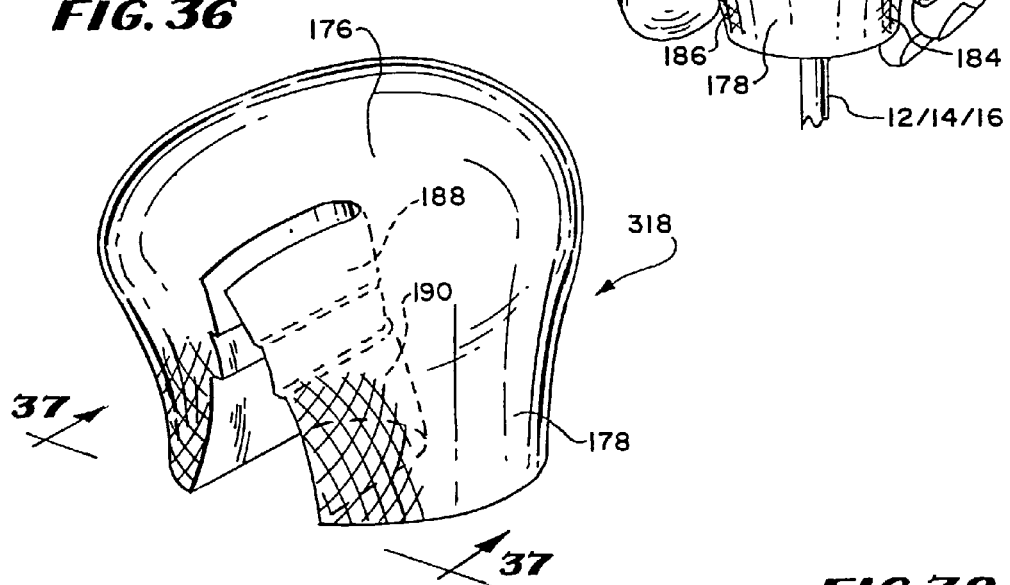
FIG. 36 is a rear side perspective view of the anvil-style handle shown in FIG. 35, showing the first and second sockets of the handle.
Figure 37:
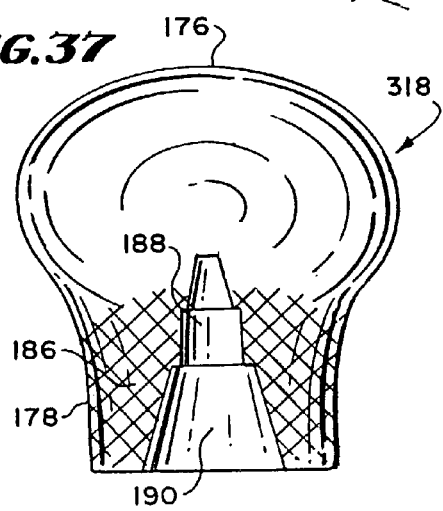
FIG. 37 is a rear elevation view of the anvil-style handle shown in FIG. 35, showing the first and second sockets of the handle.
Figure 38:
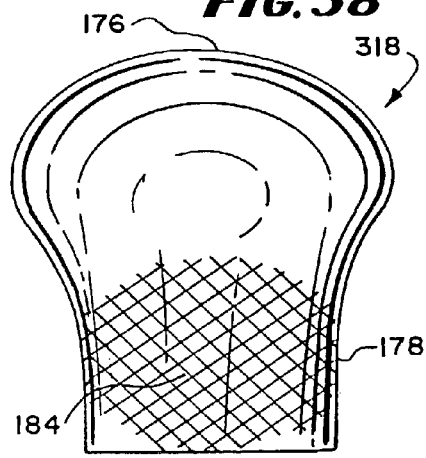
FIG. 38 is a front elevation view of the anvil-style handle shown in FIG. 35.

It should be appreciated that the sockets 80 and 86 shown in the T-shaped handle 18 in a side-by-side arrangement (see FIGS. 5 to 8), can, in an alternative embodiment, be stacked one above the other in the manner shown for the anvil handle 318 in FIG. 36. In this arrangement, the smaller first socket 80 is stacked concentrically above the larger second socket 86. The passage 92 extends along the center axis of the sockets 80 and 86, opening into the first socket 80 and thereby serving both sockets 80 and 86. This alternative construction allows central placement of all the instruments carried by the handle.

All preceding embodiments show the handle as possessing female attachment components (i.e., the sockets) to receive male handle attachment sites (i.e., the fittings) on the instruments. Of course, this arrangement can be reversed and still provide all the benefits of the invention. That is, as shown in FIG. 39, a handle 400 can carry male handle attachment sites 402 and 404 that mate in the desired running slip fit fashion with female attachment components 406, 408, and 410 carried by the instruments 412, 414, and 416, respectively. In FIG. 39, attachment site 402 uniquely mates with the attachment components 406 and 410, while attachment site 404 uniquely mates with attachment component 408. Alternatively, the handle 400 can carry one male attachment site and one female attachment component, and one instrument can likewise carry a male attachment site, while another instrument can carry a female attachment component. It should be fully appreciated that many attachment site/component combinations on the instruments and handle are possible. Regardless of the particular combination selected, the use of the handle 400 in association with the instruments 412, 414, and 416 is identical to that previously described in the context of other embodiments.

The foregoing description demonstrates the applicability of a handle made according to the invention for use in association with a wide assortment of different instruments or tools, and for use both inside and outside the medical field. The handle provides error-free coupling to different instruments or tools, and, further, uniquely allows coupling to one instrument or tool which has nested within it another instrument or tool. The shape and size of the handle can also vary significantly, limited only by the practicalities surrounding hand-held use and manipulation.

The features of the invention are set forth in the following claims.

I claim:

1. A method comprising
providing a system comprising a surgical instrument having a bore extending therethrough accommodating passage of a guide pin instrument and including a handle attachment site, a guide pin instrument sized and configured for passage through the bore of the surgical instrument, and a handle separate from the surgical instrument and the guide pin instrument including an attachment component configured to selectively engage or disengage the handle attachment site of the surgical instrument, and a passageway extending through the handle from the attachment component and accommodating passage of the guide pin instrument through the handle to accommodate sliding the handle over and relative to the guide pin instrument when selectively engaging or disengaging the attachment component and the handle attachment site,
deploying the guide pin instrument into a soft tissue region,
slidably advancing the surgical instrument over and relative to the guide pin instrument,
slidably advancing the handle over and relative to the guide pin instrument toward the surgical instrument to engage the attachment component with the handle attachment site,
manipulating the handle to manipulate the surgical instrument over and relative to the guide pin instrument in the soft tissue region, and
slidably withdrawing the handle over and relative to the guide pin instrument away from the surgical instrument to disengage the attachment component from the handle attachment site and separate the handle from the guide pin instrument.

2. A method according to claim 1
wherein the attachment component and the handle attachment site engage in a slip fit.

3. A method according to claim 1
wherein the surgical instrument comprises a cannula.

4. A method according to claim 1
wherein the surgical instrument comprises an obturator.

5. A method comprising
providing a system comprising an obturator instrument having a bore extending therethrough accommodating passage of a guide pin instrument and including an obturator handle attachment site, a cannula instrument having a bore extending therethrough accommodating passage of the obturator instrument and including a cannula handle attachment site, and a handle separate from the obturator instrument and the cannula instrument, the handle including spaced-apart first and second attachment components configured to selectively engage and disengage, respectively, the obturator handle attachment site and the cannula handle attachment site, the handle also including spaced-apart first and second passageways extending through the handle, respectively, from the first and second attachment components and accommodating passage of a guide pin instrument through the handle to accommodate sliding the handle over and relative to the guide pin instrument when selectively engaging or disengaging the respective attachment component and the respective handle attachment site, deploying a guide pin instrument into a soft tissue region, slidably advancing the obturator instrument over and relative to the guide pin instrument, slidably advancing the handle over and relative to the guide pin instrument toward the obturator instrument to engage the first attachment component with the obturator handle attachment site, manipulating the handle to manipulate the obturator instrument over and relative to the guide pin instrument in the soft tissue region, slidably withdrawing the handle over and relative to the guide pin instrument away from the obturator instrument to disengage the first attachment component from the obturator handle attachment site and separate the handle from the guide pin instrument, slidably advancing the cannula instrument over and relative to the guide pin instrument and the obturator instrument, slidably advancing the handle over and relative to the guide pin instrument toward the cannula instrument to engage the second attachment component with the cannula handle attachment site, and manipulating the handle to manipulate the cannula instrument over and relative to the guide pin instrument in the soft tissue region.

6. A method according to claim 5 wherein the first and second attachment components and the respective handle attachment sites engage in a slip fit.

7. A method according to claim 5 and further comprising slidably withdrawing the handle over and relative to the guide pin instrument away the cannula instrument to disengage the second attachment component from the cannula handle attachment site and separate the handle from the guide pin instrument.

8. A method according to claim 7 and further comprising withdrawing the obturator instrument and the guide pin instrument from the cannula instrument.

\* \* \* \* \*

UNITED STATES PATENT AND TRADEMARK OFFICE
CERTIFICATE OF CORRECTION

PATENT NO. : 7,063,703 B2
APPLICATION NO. : 10/227714
DATED : June 20, 2006
INVENTOR(S) : Michael L. Reo It is certified that error appears in the above-identified patent and that said Letters Patent is hereby corrected as shown below:

Column 16, line 18, after "handle" insert -- away --

Column 16, line 63, after "respectively," insert -- away --

Column 18, line 12, after "away" insert -- from --

Signed and Sealed this

Third Day of April, 2007

JON W. DUDAS
*Director of the United States Patent and Trademark Office*